United States Patent
Liu et al.

(10) Patent No.: US 11,292,193 B2
(45) Date of Patent: Apr. 5, 2022

(54) HIGH-THROUGHPUT AND HIGH-PRECISION PHARMACEUTICAL ADDITIVE MANUFACTURING SYSTEM

(71) Applicant: Triastek, Inc., Nanjing (CN)

(72) Inventors: Haili Liu, Nanjing (CN); Feihuang Deng, Nanjing (CN); Wei Wu, Nanjing (CN); Renjie Li, Nanjing (CN); Senping Cheng, Nanjing (CN); Xiaoling Li, Dublin, CA (US)

(73) Assignee: Triastek, Inc., Nanjing (CN)

( * ) Notice: Subject to any disclaimer, the term of this patent is extended or adjusted under 35 U.S.C. 154(b) by 0 days.

(21) Appl. No.: 17/180,565

(22) Filed: Feb. 19, 2021

(65) Prior Publication Data

US 2021/0178677 A1   Jun. 17, 2021

Related U.S. Application Data

(63) Continuation of application No. PCT/CN2020/105868, filed on Jul. 30, 2020.

(30) Foreign Application Priority Data

Aug. 20, 2019 (WO) ................. PCT/CN2019/101621

(51) Int. Cl.
*B29C 64/209* (2017.01)
*B33Y 10/00* (2015.01)
(Continued)

(52) U.S. Cl.
CPC .......... *B29C 64/209* (2017.08); *A61K 9/2095* (2013.01); *B29C 64/245* (2017.08);
(Continued)

(58) Field of Classification Search
None
See application file for complete search history.

(56) References Cited

U.S. PATENT DOCUMENTS

| 5,121,329 A | 6/1992 | Crump |
| 5,303,141 A | 4/1994 | Batchelder |

(Continued)

FOREIGN PATENT DOCUMENTS

| CN | 104260349 A | 1/2015 |
| CN | 104552949 A | 4/2015 |

(Continued)

OTHER PUBLICATIONS

Cheng et al., WO 2018210183, English Machine Translation from WIPO website via Google (Year: 2018).*

(Continued)

*Primary Examiner* — Colin W. Slifka
(74) *Attorney, Agent, or Firm* — Morrison & Foerster, LLP

(57) ABSTRACT

The present disclosure relates generally to manufacturing pharmaceutical products using additive manufacturing technology. An exemplary printing system comprises: a material supply module for receiving a set of printing materials; a flow distribution module comprising a flow distribution plate, wherein the material supply module is configured to transport a single flow corresponding to the set of printing materials to the flow distribution plate; wherein the flow distribution plate comprises a plurality of channels for dividing the single flow into a plurality of flows; a plurality of nozzles, wherein the plurality of nozzles comprises a plurality of needle-valve mechanisms; one or more controllers for controlling the plurality of needle-valve mechanisms to dispense the plurality of flows based on a plurality of nozzle-specific parameters; and a printing platform configured to receive the dispensed plurality of flows, wherein the printing platform is configured to move to form a batch of the pharmaceutical product.

30 Claims, 18 Drawing Sheets

(51) Int. Cl.
*B33Y 30/00* (2015.01)
*B33Y 80/00* (2015.01)
*B29C 64/245* (2017.01)
*B33Y 70/10* (2020.01)
*A61K 9/20* (2006.01)

(52) U.S. Cl.
CPC .............. *B33Y 10/00* (2014.12); *B33Y 30/00* (2014.12); *B33Y 70/10* (2020.01); *B33Y 80/00* (2014.12)

(56) References Cited

U.S. PATENT DOCUMENTS

| | | |
|---|---|---|
| 5,529,471 A | 6/1996 | Khoshevis |
| 5,936,861 A | 8/1999 | Jang et al. |
| 6,986,739 B2 | 1/2006 | Warren |
| 9,233,506 B2 | 1/2016 | Leavitt |
| 9,297,845 B2 | 3/2016 | Mathur |
| 9,944,016 B2 | 4/2018 | Lewicki |
| 9,974,607 B2 | 5/2018 | Stone |
| 10,011,073 B2 | 7/2018 | Bheda |
| 10,143,626 B2 | 12/2018 | Li |
| 10,201,503 B1 | 2/2019 | Li |
| 10,258,575 B2 | 4/2019 | Li |
| 10,350,822 B1 | 7/2019 | Deng |
| 10,363,220 B2 | 7/2019 | Li |
| 10,624,857 B2 | 4/2020 | Li |
| 10,973,767 B2 | 4/2021 | Li |
| 2004/0253365 A1 | 12/2004 | Warren et al. |
| 2014/0116217 A1 | 5/2014 | Hashish |
| 2015/0352787 A1 | 12/2015 | Humbert et al. |
| 2016/0074938 A1 | 3/2016 | Kitani et al. |
| 2016/0075091 A1 | 3/2016 | Cable |
| 2016/0288427 A1 | 10/2016 | Foley et al. |
| 2016/0303802 A1 | 10/2016 | Meshorer |
| 2016/0354315 A1 | 12/2016 | Li |
| 2017/0008230 A1 | 1/2017 | Yuyama |
| 2017/0050375 A1 | 2/2017 | Tyler |
| 2017/0120513 A1 | 5/2017 | Brennan |
| 2017/0217088 A1 | 8/2017 | Boyd, IV et al. |
| 2017/0360714 A1 | 12/2017 | Church |
| 2018/0001565 A1 | 1/2018 | Hocker |
| 2018/0049993 A1 | 2/2018 | Blaesi et al. |
| 2018/0056602 A1 | 3/2018 | Susnjara |
| 2018/0111306 A1* | 4/2018 | Mandel .............. B29C 48/266 |
| 2018/0116911 A1 | 5/2018 | Li |
| 2018/0184702 A1 | 7/2018 | Moh |
| 2018/0311167 A1 | 11/2018 | Li |
| 2018/0318929 A1 | 11/2018 | Matthews |
| 2018/0339448 A1 | 11/2018 | Fan et al. |
| 2018/0339455 A1 | 11/2018 | Cohen |
| 2019/0001574 A1 | 1/2019 | Yackabonis |
| 2019/0022934 A1 | 1/2019 | Kobe et al. |
| 2019/0047225 A1 | 2/2019 | Luo |
| 2019/0192440 A1 | 6/2019 | Li |
| 2019/0202126 A1 | 7/2019 | Hutchinson et al. |
| 2019/0209468 A1 | 7/2019 | Deng |
| 2019/0209482 A1 | 7/2019 | Li |
| 2019/0321299 A1 | 10/2019 | Li |
| 2020/0030491 A1 | 1/2020 | Weisman et al. |
| 2020/0315971 A1 | 10/2020 | Li |
| 2020/0338009 A1 | 10/2020 | Li |
| 2021/0077410 A1 | 3/2021 | Deng et al. |
| 2021/0078244 A1 | 3/2021 | Deng et al. |
| 2021/0128479 A1 | 5/2021 | Cheng et al. |
| 2021/0196638 A1 | 7/2021 | Deng et al. |
| 2021/0205226 A1 | 7/2021 | Li |

FOREIGN PATENT DOCUMENTS

| | | |
|---|---|---|
| CN | 204414597 U | 6/2015 |
| CN | 104742375 A | 7/2015 |
| CN | 105313332 A | 2/2016 |
| CN | 105365221 A | 3/2016 |
| CN | 105666640 A | 6/2016 |
| CN | 105711094 A | 6/2016 |
| CN | 205343831 U | 6/2016 |
| CN | 105856562 A | 8/2016 |
| CN | 105965888 A | 9/2016 |
| CN | 106079434 A | 11/2016 |
| CN | 106255583 A | 12/2016 |
| CN | 106622413 A | 5/2017 |
| CN | 106926444 A | 7/2017 |
| CN | 107019676 A | 8/2017 |
| CN | 206436522 U | 8/2017 |
| CN | 107718560 A | 2/2018 |
| CN | 108215153 A | 6/2018 |
| CN | 108215154 A | 6/2018 |
| CN | 207579101 U * | 7/2018 |
| CN | 207669820 U | 7/2018 |
| CN | 108582765 A | 9/2018 |
| CN | 207874876 U | 9/2018 |
| CN | 207901677 U | 9/2018 |
| CN | 109228325 A | 1/2019 |
| CN | 208768826 U | 4/2019 |
| CN | 109719944 A | 5/2019 |
| CN | 208812559 U | 5/2019 |
| CN | 105690762 A | 6/2019 |
| CN | 109895390 A | 6/2019 |
| CN | 108215153 B | 8/2019 |
| CN | 110507637 A | 11/2019 |
| CN | 108215154 B | 1/2020 |
| EP | 3626439 A1 | 3/2020 |
| KR | 20190031959 A | 3/2019 |
| WO | 2015065936 A2 | 5/2015 |
| WO | 2015129733 A1 | 9/2015 |
| WO | 2015171352 A1 | 11/2015 |
| WO | 2016097911 A1 | 6/2016 |
| WO | 2016126962 A1 | 8/2016 |
| WO | 2016185215 A1 | 11/2016 |
| WO | 2016192680 A1 | 12/2016 |
| WO | 2017193099 A1 | 11/2017 |
| WO | 2018100444 A2 | 6/2018 |
| WO | 2018137686 A1 | 8/2018 |
| WO | 2018210183 A1 | 11/2018 |
| WO | 2018137686 A9 | 12/2018 |
| WO | 2018100444 A3 | 2/2019 |
| WO | 2019137199 A1 | 7/2019 |
| WO | 2019137200 A1 | 7/2019 |
| WO | 2019137333 A1 | 7/2019 |
| WO | 2021031824 A1 | 2/2021 |
| WO | 2021042865 A1 | 3/2021 |
| WO | 2021164660 A1 | 8/2021 |

OTHER PUBLICATIONS

Yang et al., CN 207579101, English Translation from WIPO website (note that the version supplied is a Google English translation on the WIPO website) (Year: 2018).*
Goyanes, A. et al. (2015). "3D Printing of Medicines: Engineering Novel Oral Devices with Unique Design and Drug Release Characteristics," Molecular Pharmaceutics 12(11):4077-4084, 8 pages.
International Preliminary Report on Patentability, dated Nov. 19, 2019, for PCT Application No. PCT/CN2018/086489, filed May 11, 2018, 1 page. English Translation.
International Search Report and Written Opinion, dated Mar. 29, 2019, for PCT/CN2019/070634, filed Jan. 7, 2019, 11 pages.
International Search Report and Written Opinion, dated Nov. 3, 2020, for PCT/CN2020/105868, filed Jul. 30, 2020, 11 pages.
International Search Report, dated Jul. 19, 2018, for PCT Application No. PCT/CN2018/086489, filed May 16, 2017, 2 pages. English Translation.
Poh, P.S.P. et al. (Dec. 15, 2016, e-pub. Aug. 1, 2016). "Polylactides in Additive Biomanufacturing," Advanced Drug Delivery Reviews 107:228-246.
Skylar-Scott, M.A. (Nov. 14, 2019, e-pub. Nov. 13, 2019). "Voxelated Soft Matter via Multimatenal Multinozzle 3D Printing," Nature 575(7782):330-335.
U.S. Appl. No. 16/614,301, Senping et al., filed Nov. 15, 2019. (Copy not submitted herewith pursuant to the waiver of 37 C.F.R. § 1.98(a)(2)(iii) issued by the Office dated Sep. 21, 2004).

(56) References Cited

OTHER PUBLICATIONS

Written Opinion of the International Searching Authority Report, dated Jul. 19, 2018, for PCT Application No. PCT/CN2018/086489, filed May 11, 2018, 4 pages. English Translation.

International Search Report and Written Opinion, dated May 12, 2021, for PCT/CN2021/076280, filed Feb. 9, 2021, 9 pages.

Zhang, J. et al. (2017, e-pub. Dec. 23, 2016). "Coupling 3D Printing With Hot-Melt Extrusion to Produce Controlled-Release Tablets," International Journal of Pharmaceutics 519:186-197.

International Search Report and Written Opinion, dated Aug. 27, 2021, for PCT Application No. PCT/CN2021/098797, filed Jun. 8, 2021, 8 pages.

* cited by examiner

1030

- MOUNTING A PRINTING PLATE ONTO A PRINTING PLATFORM
  1032
  - MOVING THE PLATFORM TO A RECEIVING POSITION
    1034
  - DETERMINING WHETHER THE PLATE IS ALIGNED WITH THE PLATFORM
    1036
  - COUPLING THE PLATE AND THE PLATFORM
    1038

- IDENTIFYING A PORTION OF PRINTING INSTRUCTIONS BASED ON PROGRESS DATA
  1040

- PRINTING BASED ON THE IDENTIFIED PORTION OF PRINTING INSTRUCTIONS
  1042

- DETERMINING WHETHER PRINTING IS COMPLETE BASED ON THE IDENTIFIED PORTION OF PRINTING INSTRUCTIONS
  1044

- RECORDING PROGRESS DATA
  1046

- DISMOUNTING THE PLATE FROM THE PLATFORM
  1048

FIG. 10B

HIGH-THROUGHPUT AND HIGH-PRECISION PHARMACEUTICAL ADDITIVE MANUFACTURING SYSTEM

CROSS REFERENCE TO RELATED APPLICATIONS

This application is a continuation application of International Application No. PCT/CN2020/105868, filed on Jul. 30, 2020, which claims the priority benefit of International Application No. PCT/CN2019/101621, filed on Aug. 20, 2019, the entire contents of both are incorporated herein by reference for all purposes.

FIELD OF INVENTION

The present disclosure relates generally to additive manufacturing technology, and more specifically to high-throughput and high-precision 3D printing techniques for manufacturing pharmaceutical dosage units (e.g., tablets caplets, printlets).

BACKGROUND

Additive manufacturing, also referred to as three-dimensional printing ("3D printing"), is a rapid prototyping technology involving processes in which material is joined or solidified to manufacture a three-dimensional object. Specifically, materials are added together (such as liquid molecules or powder grains being fused together), typically layer by layer, based on a digital model. A computer system operates the additive manufacturing system, and controls material flow and movement of a printing nozzle until the desired shape is formed. Currently, 3D printing technology includes photocuring techniques, powder bonding techniques, and fused deposition modeling (FDM) techniques.

In an FDM process, material in the form of a filament is fed through a heated nozzle, which melts the material onto a surface. The surface or the heated nozzle can move to dispense the molten material into a set shape, as instructed by the computer system. Other additive manufacturing methods utilize non-filamentous materials that are molten and pressurized before being dispensed through a printing nozzle, but such methods often result in undesirable stringing from the printing nozzle, particular when the molten material is of high viscosity.

There are several challenges with adapting techniques such as FDM for the use of manufacturing pharmaceutical dosage units (e.g., tablets, caplets, printlets): achieving high throughput, achieving high precision/consistency, and printing pharmaceutical dosage units having complex structures and compositions. For example, a single-nozzle printing device or a multi-nozzle printing device can only achieve relatively low throughput. On the other hand, systems providing parallel printing by running multiple printing devices simultaneously are also deficient, as the multiple printing devices introduce inconsistency and low precision among the printed units (e.g., in volume, shape, weight, and/or composition). Such systems are also expensive to manufacture and maintain, as well as inefficient and complex to operate.

In particular, the printing materials required in the pharmaceutical context tend to be of high viscosity and are associated with low printing pressure. Further, when multiple types of printing material are involved in the printing process, nozzles dispensing these different types of printing material need to be operating in a coordinated manner (e.g., opened and closed alternately). Traditional 3D printing systems cannot coordinate the operation of multiple nozzles and control the release of multiple types of material in a precise and consistent manner. Thus, traditional 3D printing systems cannot maintain a high level of consistency among the pharmaceutical dosage units outputted by the nozzles, in the same batch or across multiple batches. The above-described challenges are compounded if the pharmaceutical unit to be manufactured is composed of different materials arranged in a particular structure (e.g., multiple inner parts coated with a shell).

Further, configuring multiple 3D printers to work together to produce a batch of pharmaceutical dosage units does not produce satisfactory results when conventional 3D printing techniques are used. Specifically, inconsistencies among the multiple 3D printers (e.g., in both hardware configuration and software configuration) can cause the end product to be inconsistent and thus fail to meet the quality standards. Further, system involving the coordination among multiple 3D printers are generally inefficient to operate and expensive to maintain.

Thus, there is a need for systems and methods for 3D printing pharmaceutical dosage units (e.g., tablets caplets, printlets) in an accurate, precise, and cost-efficient manner, while maintaining high throughput over time. There is also a need for a system that can coordinate the operations of multiple 3D printers to print a batch of pharmaceutical dosage units.

BRIEF SUMMARY

An exemplary system for creating pharmaceutical products by additive manufacturing, comprises: a material supply module for receiving a set of printing materials; a flow distribution module comprising a flow distribution plate, wherein the material supply module is configured to transport a single flow corresponding to the set of printing materials to the flow distribution plate; wherein the flow distribution plate comprises a plurality of channels for dividing the single flow into a plurality of flows; a plurality of nozzles; and one or more controllers for controlling the plurality of nozzles to dispense the plurality of flows based on a plurality of nozzle-specific parameters.

In some embodiments, the system further comprises a printing platform configured to receive the dispensed plurality of flows, wherein the printing platform is configured to move to form a batch of the pharmaceutical product.

In some embodiments, the material supply module is configured to heat the received set of printing materials.

In some embodiments, the material supply module is configured to plasticize the received set of printing materials.

In some embodiments, the material supply module comprises a piston mechanism, a screw mechanism, a screw pump mechanism, a cogwheel mechanism, a plunger pump mechanism or any combination thereof.

In some embodiments, the plurality of channels forms a first juncture configured to dividing the single flow into two flows.

In some embodiments, wherein the plurality of channels forms a second juncture and a third juncture configured to divide the two flows into 4 flows.

In some embodiments, the first juncture is positioned higher than the second juncture and the third juncture.

In some embodiments, the first juncture, the second juncture, and the third juncture are positioned on a same plane.

In some embodiments, the flow distribution plate is splittable into a plurality of components, wherein the plurality of components are configured to be held together via one or more screws.

In some embodiments, a nozzle of the plurality of nozzles comprises a heater.

In some embodiments, a nozzle of the plurality of nozzles comprises a thermal isolation structure.

In some embodiments, the plurality of nozzles comprises a plurality of needle-valve mechanisms.

In some embodiments, a needle-valve mechanism of the plurality of needle-valve mechanisms comprises: a feed channel extending through the respective nozzle, wherein the feed channel is tapered at a distal end of the nozzle; and a needle, wherein a distal end of the needle is configured to be in contact and seal the feed channel when the needle-valve mechanism is in a closed position, and wherein the distal end of the needle is configured to be retracted to allow a flow of printing materials to be dispensed.

In some embodiments, movement of the needle is driven by one or more actuators.

In some embodiments, the one or more actuators include a linear motor.

In some embodiments, movement of the needle is controlled manually.

In some embodiments, the needle is a first needle, the plurality of nozzles comprises a single plate coupled to the first needle and a second needle, and wherein movement of the single plate causes movement of the first needle and the second needle.

In some embodiments, a parameter of the plurality of nozzle-specific parameters comprises an amount of opening of a respective nozzle.

In some embodiments, the one or more controllers are configured to adjust the amount of opening of the respective nozzle based on a weight of a unit in the batch corresponding to the respective nozzle.

In some embodiments, the one or more controllers are configured to adjust the amount of opening of the respective nozzle based one or more machine learning algorithms.

In some embodiments, the one or more controllers are configured to control temperature or pressure at the plurality of the nozzles.

In some embodiments, the temperature is controlled via a temperature control device comprising one or more heating devices, one or more cooling devices, or a combination thereof.

In some embodiments, a temperature at the plurality of the nozzles is higher than a temperature at the materials supply module.

In some embodiments, a temperature at the plurality of the nozzles is higher than a temperature at the flow distribution plate.

In some embodiments, the one or more controllers are configured to control a feeding speed of the set of printing materials.

In some embodiments, the plurality of nozzles is a first plurality of nozzles, the printing system further comprising a second plurality of nozzles configured to dispense a different set of materials, wherein the printing system is configured to switch between the first plurality of nozzles and the second plurality of nozzles to print the batch.

In some embodiments, the pharmaceutical unit is a tablet.

An exemplary computer-enabled method for creating pharmaceutical products by additive manufacturing, comprises: receiving a plurality of unit measurements corresponding to a plurality of pharmaceutical dosage units, wherein the plurality of pharmaceutical dosage units are generated using a plurality of nozzles of an additive manufacturing system; determining whether a sum of the plurality of unit measurements differs from a target batch measurement by more than a predefined threshold; in accordance with a determination that the sum differs from the target batch measurement by more than the predefined threshold, adjusting one or more nozzles of the plurality of nozzles based on an average of the plurality of unit measurements; in accordance with a determination that the sum does not differ from the target batch measurement by more than the predefined threshold, adjusting one or more nozzles of the plurality of nozzles based on a target unit measurement.

In some embodiments, the plurality of pharmaceutical unit is a plurality of tablets.

In some embodiments, the unit measurements are weight measurements of the plurality of pharmaceutical dosage units.

In some embodiments, the unit measurements are volume measurements of the plurality of pharmaceutical dosage units.

In some embodiments, the unit measurements are composition measurements of the plurality of pharmaceutical dosage units.

In some embodiments, the method further comprises: in accordance with a determination that the sum differs from the target batch measurement by more than the predefined threshold, adjusting one or more operation parameters of the additive manufacturing system.

In some embodiments, the one or more operation parameters include temperature.

In some embodiments, the one or more operation parameters include pressure.

In some embodiments, the one or more operation parameters include a speed of feeding printing materials.

In some embodiments, the predefined threshold is between +/−0.5% to +/−5%.

In some embodiments, the method further comprises, after adjusting one or more nozzles of the plurality of nozzles based on a target unit measurement, printing a new batch; determining whether a weight of an unit in the new batch differs from the target unit measurement by more than a second predefined threshold; in accordance with a determination that the weight of the unit in the new batch differs from the target unit measurement by more than the second predefined threshold, adjusting one or more operation parameters of the additive manufacturing system.

In some embodiments, the one or more operation parameters include temperature.

In some embodiments, the one or more operation parameters include an amount of opening of a nozzle.

In some embodiments, the second predefined threshold is less than 5%.

An exemplary method for manufacturing pharmaceutical products by additive manufacturing comprises: receiving, using a material supply module, a set of printing materials; transporting, using the material supply module, a single flow corresponding to the set of printing materials to a flow distribution plate, wherein the flow distribution plate comprises a plurality of channels; dividing, via the plurality of channels of the flow distribution plate, the single flow into a plurality of flows; causing a plurality of nozzles to dispense the plurality of flows based on a plurality of nozzle-specific parameters.

An exemplary non-transitory computer-readable storage medium stores one or more programs, the one or more programs comprising instructions, which when executed by one or more processors of an electronic device having a display, cause the electronic device to: receive a plurality of weight measurements corresponding to a plurality of pharmaceutical dosage units, wherein the plurality of pharmaceutical dosage units are generated using a plurality of nozzles of a 3D printing system; determine whether a sum of the plurality of weight measurements differs from a target batch weight by more than a predefined threshold; in accordance with a determination that the sum differs from the target batch weight by more than the predefined threshold, adjust one or more nozzles of the plurality of nozzles based on an average weight measurement of the plurality of weight measurements; in accordance with a determination that the sum does not differ from the target batch weight by more than the predefined threshold, adjust one or more nozzles of the plurality of nozzles based on a target weight measurement.

In some embodiments, an exemplary system for manufacturing a plurality of pharmaceutical products by additive manufacturing comprises a first printing station comprising: a first printing platform; and a first plurality of nozzles; a second printing station comprising: a second printing platform; and a second plurality of nozzles; a plate transport mechanism; a printing plate; wherein the system is configured to: while the printing plate is positioned on the first printing platform, determining whether printing of a first portion of each pharmaceutical product in the plurality of pharmaceutical products is complete at the first printing station; in accordance with a determination that the printing of the first portion is complete at the first printing station, identifying the second printing station; transporting the printing plate from the first printing platform to the second printing platform via the plate transport mechanism; and causing printing of a second portion of each pharmaceutical product in the batch of pharmaceutical products at the second printing station.

In some embodiments, the system further comprises two conveyors, wherein the system is configured to transport the printing plate via the plate transport mechanism along one of the two conveyors.

In some embodiments, the printing of the first portion at the first printing station is based on a first coordinate system associated with the first printing station, and the printing of the second portion at the second printing station is based on a second coordinate system associated with the second printing station.

In some embodiments, the system is configured to: obtaining a first relative positioning between the first printing platform and the first plurality of nozzles; obtaining a second relative positioning between the second printing platform and the second plurality of nozzles; calculating a plurality of offset values based on the first relative positioning and the second relative positioning; determining at least one of the first coordinate system and the second coordinate system based on the plurality of offset values.

In some embodiments, the first relative positioning comprises a first x-axis value and a first y-axis value, and wherein the second relative positioning comprises a second x-axis value and a second y-axis value.

In some embodiments, the plurality of offset values comprises: a difference value between the first x-axis value and the second x-axis value and a difference value between the first y-axis value and the second y-axis value.

In some embodiments, obtaining the first relative positioning comprises: while the printing plate is positioned on the first printing platform, measuring the first x-axis and the first y-axis value based on one or more retractable sensors placed on the first printing station.

In some embodiments, obtaining the first relative positioning comprises: while the printing plate is positioned on the first printing platform, measuring the first x-axis and the first y-axis value based on one or more laser sensors placed on the first printing station.

In some embodiments, obtaining the first relative positioning comprises: moving the first printing platform on the x-axis until it comes in contact with a first sensor on the first printing station; and moving the second printing platform on the y-axis until it comes in contact with a second sensor on the first printing station.

In some embodiments, determining the first coordinate system comprises: determining a zero point on the z axis.

In some embodiments, the zero point comprises a z-axis position where a plate placed on the first printing platform comes in contact with first plurality of nozzles.

In some embodiments, determining the zero point is performed using a plug gauge.

In some embodiments, determining the zero point comprises: elevating the first printing platform; determining, using a sensor coupled to the first printing platform, whether a resistance force above a predefined threshold is detected; in accordance with a determination that the resistance force above the predefined threshold is detected, pausing elevating the first printing platform and determining the zero point based on a current z-axis position of the first printing platform; in accordance with a determination that the resistance force above the predefined threshold is not detected, continuing elevating the first printing platform.

In some embodiments, determining the zero point comprises: affixing a sensor having a retractable portion to the first printing platform, wherein the retractable portion is protruded out of the first printing platform; placing an object over the sensor such that the protruded portion of the sensor is retracted; recording a retracted position of the sensor; while elevating the first printing platform, determining whether the retracted position of the sensor is detected; and in accordance with a determination that the retracted position is detected, determining the zero point based on a current z-axis position of the first printing platform;

In some embodiments, the first plurality of nozzles is configured to dispense a first type of printing material, and wherein the second plurality of nozzles is configured to dispense a second type of printing material.

In some embodiments, the batch of pharmaceutical products comprises a batch of tablets; the first portion of each pharmaceutical product comprises an outer portion of the respective tablet; and the second portion of each pharmaceutical product comprises an inner portion of the respective tablet.

In some embodiments, the batch of pharmaceutical products comprises a batch of tablets; the first portion of each pharmaceutical product comprises a lower portion of the respective tablet; and the second portion of each pharmaceutical product comprises an upper portion of the respective tablet.

In some embodiments, determining whether printing of the first portion of each pharmaceutical product in the batch of pharmaceutical products is complete at the first printing station comprises: receiving, at the plate transport mechanism, a status of the first printing station; and determining, at the plate transport mechanism, whether the printing is complete based on the status of the first printing station.

In some embodiments, the system is further configured to: after printing of the first portion of each pharmaceutical product is complete, recording progress data associated with the printing plate.

In some embodiments, the progress data comprises a current height of the batch of pharmaceutical products.

In some embodiments, the progress data comprises the identified second printing station.

In some embodiments, the system is configured to transmit the recorded progress data from the first printing station to the plate transport mechanism.

In some embodiments, identifying the second printing station is based a set of printing instructions associated with the pharmaceutical products.

In some embodiments, identifying the second printing station is based the second portion to be printed.

In some embodiments, identifying the second printing station is based printing material associated with the second portion to be printed.

In some embodiments, identifying the second printing station is based a status of the second printing station.

In some embodiments, transporting the printing plate from the first printing platform to the second printing platform via the plate transport mechanism comprises: demounting the printing plate from the first platform; moving the printing plate onto the plate transport mechanism; and moving the plate transport mechanism along a channel based on a location associated with the second printing station.

In some embodiments, demounting the printing plate from the first platform comprises deactivating an electromagnetic component.

In some embodiments, causing printing of the second portion of each pharmaceutical product in the batch of pharmaceutical products at the second printing station comprises: updating the status of the second printing station as busy.

In some embodiments, causing printing of the second portion of each pharmaceutical product in the batch of pharmaceutical products at the second printing station comprises: identifying a portion of printing instructions based on progress data associated with the printing plate.

In some embodiments, the progress data comprises a current height of the batch of pharmaceutical products on the printing plate.

In some embodiments, the progress data is transmitted from the plate transport mechanism to the second printing station.

In some embodiments, the system further comprises a controller associated with the first printing station, a controller associated with the second printing station, or any combination thereof.

In some embodiments, the system further comprises a controller associated with the plate transport mechanism.

In some embodiments, the system further comprises a third printing station.

DESCRIPTION OF THE FIGURES

FIG. 10B depicts an exemplary process for 3D printing pharmaceutical dosage units using a multi-station system, according to some embodiments.

DETAILED DESCRIPTION

Figure 1A:
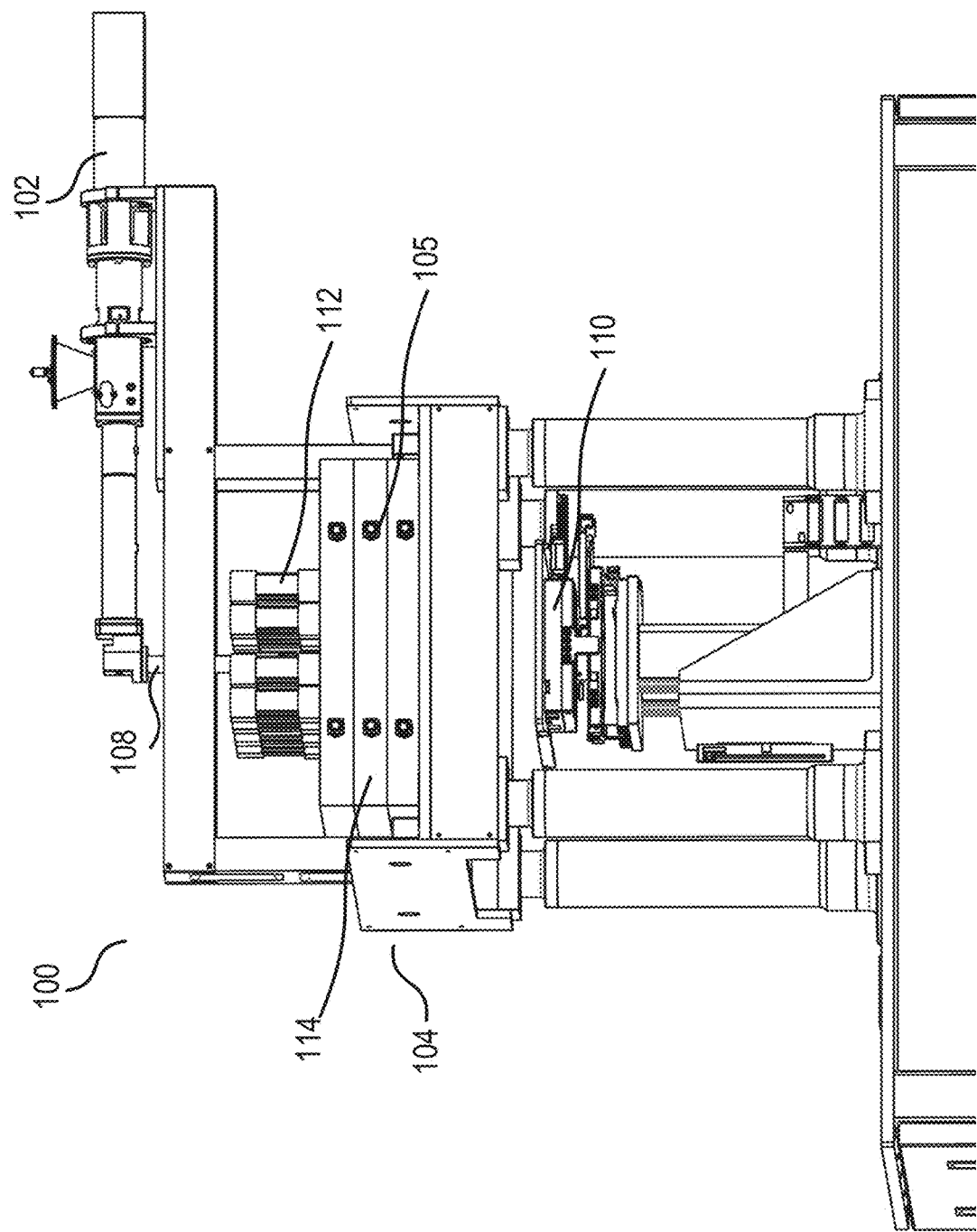
FIG. 1A depicts a schematic view of an exemplary additive manufacturing system, according to some embodiments of a present invention.

Described herein are apparatuses, devices, systems, methods, and non-transitory storage media for additive manufacturing (e.g., 3D printing) pharmaceutical dosage units (e.g., tablets caplets, printlets) in an accurate, precise, and cost-efficient manner, while maintaining high throughput over time. According to the some embodiments, a printing system leverages a flow distribution module for dividing a single flow of printing material(s) into a plurality of flows. The plurality of flows are dispensed by a plurality of nozzles in a precisely controlled manner to 3D print a batch of pharmaceutical dosage units (e.g., tablets caplets, printlets), thus achieving consistency among the units in a single batch and across multiple batches, while maintaining high-throughput.

Further, the printing system comprises an environment (e.g., a closed environment such as a constant temperature oven, an open environment such as a printing platform) for additive manufacturing (e.g., 3D printing) pharmaceutical dosage units. A plurality of close-loop control systems are used to control temperature, pressure, flow, weight, volume, and other relevant parameters in the environment in multiple stages of the manufacturing process. In particular, control systems and methods are implemented to adjust the opening of the nozzles, specifically, the opening of the needle-valve mechanisms at the nozzles, in a precise manner to ensure consistency among outputs of the nozzles. In some embodiments, the inconsistency in unit weight (i.e., inconsistency among weights of units in the same batch) are smaller than 10% (e.g., 1%, 2%, 3%, 4%, 5%, 6%, 7%, 8%, 9%, 9.5%, 10%). In some embodiments, the inconsistency in batch weight (i.e., inconsistency among weights of batches) are smaller than 10% (e.g., 1%, 2%, 3%, 4%, 5%, 6%, 7%, 8%, 9%, 9.5%, 10%).

Based different types of printing materials and the compositions required, the system can adjust the control parameters. This way, the printing system can be used to manufacture a variety of high-quality pharmaceutical dosage units.

In some embodiments, the material is non-filamentous (e.g., powder, pellet, or liquid). In some embodiments, the material has a viscosity of 0.01-10000 Pa·s when dispensed from the system. For example, the material has a viscosity of about 100 Pa·s or more when dispensed from the device. In some embodiments, the material has a viscosity of about 400 Pa·s or more when dispensed from the device. In some embodiments, the material melts at about 50° C. to about 400° C. In some embodiments, the material is dispensed from the nozzle at a temperature of about 50° C. to about 400° C. In some embodiments the material is dispensed from the nozzle at a temperature of about 90° C. to about 300° C.

In some embodiments, the printing system comprises multiple printing stations. Each printing station can be used to print a portion (e.g., the shells, the lower halves, the top halves) of a batch of pharmaceutical dosage units. Further, the multiple printing stations can work in parallel such that multiple batchs of pharmaceutical dosage units can be printed at the same time. In some embodiment, a single FDM multi-station system can manufacture 3,000-5,000 pharmaceutical units (e.g., tablets) per day. In some embodiments, the system minimizes inconsistencies among pharmaceutical units in the same patch and in different patches to ±2.5% (e.g., in weight, in volume). In some embodiments, the multi-station system is easy to clean and maintain, thus in compliance with requirements for standardization production of pharmaceutical products.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Although the following description uses terms "first," "second," etc. to describe various elements, these elements should not be limited by the terms. These terms are only used to distinguish one element from another. For example, a first nozzle could be termed a second nozzle, and, similarly, a second nozzle could be termed a first nozzle, without departing from the scope of the various described embodiments. The first nozzle and the second nozzle are both nozzles, but they are not the same nozzle.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Figure 1B:
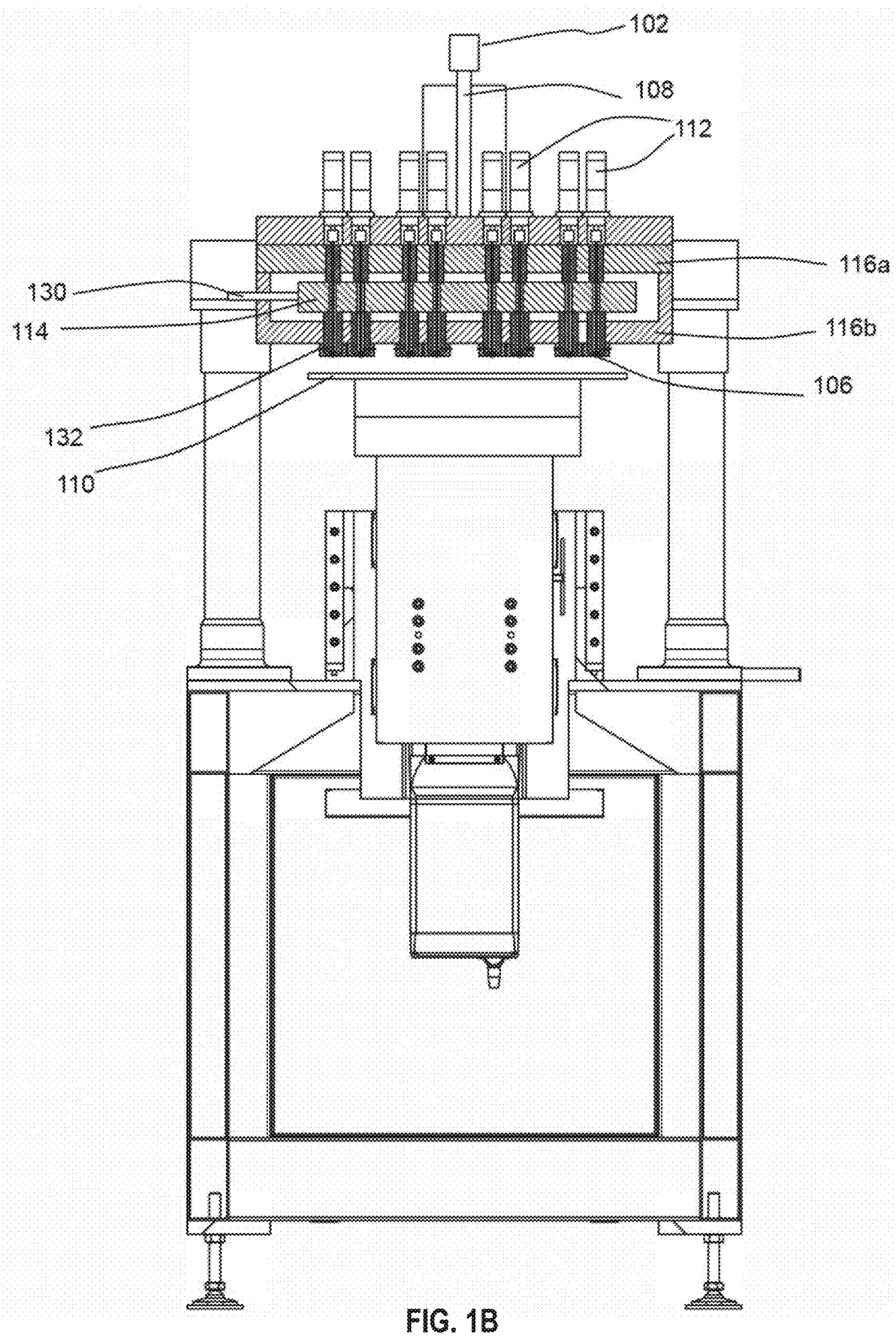
FIG. 1B depicts a schematic view of an exemplary additive manufacturing system, according to some embodiments of a present invention.

FIG. 1A depicts a schematic view of an exemplary additive manufacturing system (e.g., 3D printing system) 100, according to some embodiments of the present invention. The system 100 comprises material supply module 102 for transporting a set of printing material(s) to a flow distribution module 104. The flow distribution module 104 comprises a flow distribution plate having branched channels (not depicted) configured to divide a single flow of the printing materials (e.g., supplied by the material supply module) into a plurality of flows. In some embodiments, the flow distribution module 104 can divide a single flow into 2 flows, which are divided into 4 flows, which are divided into 8 flows, which are divided into 16 flows, which are divided into 32 flows. In some embodiments, the flow distribution module can divide a single flow directly into 2 flows, 3 flows, 4 flows, 5 flows . . . or n flows. In some embodiments, the flow distribution module can divide a single flow into 3 flows, which are divided into 9 flows, which are divided into 27 flows. With reference to FIG. 1B, the plurality of flows can be dispensed by an array of nozzles 106 of the system 100, respectively, to generate 3D-printed pharmaceutical dosage units (e.g., tablets caplets, printlets) over the printing platform 110.

The material supply module 102 is configured to preprocess the set of printing material(s) before transporting it to the flow distribution module 104. In some embodiments, the preprocessing comprises melting and pressurizing the printing material(s) based on predetermined settings (e.g., to a target range of temperature, to a target range of pressure). The preprocessed material is then transported via a supply channel 108 to the flow distribution module 104. In some embodiments, a continuous flow of printing material(s) is supplied to the flow distribution module 104 via the supply channel 108.

In some embodiments, the material supply module 102 comprises one or more heaters configured to melt the printing material(s). In some embodiments, the material supply module comprises one or more temperature sensors configured to detect the temperature of the melted printing material(s) within the material supply module 102. In some embodiments, the one or more temperature sensors are connected to a computer system that operates the one or more heaters in response to a temperature reported by the one or more temperature sensors.

In some embodiments, one or more pressure sensors are connected to a computer system that operates the material supply module to pressurize the printing material(s) to a desired pressure in response to the pressure reported by the pressure sensors. In some embodiments, the pressure of the printing is within about 0.05 MPa of the desired pressure. In some embodiments, the material supply module comprises a piston mechanism, a screw mechanism (single-screw, twin-screw, 3-screw, 4-screw, 5-screw, 8-screw), a screw pump mechanism, a cogwheel mechanism, a plunger pump mechanism (e.g., a valve-less measuring pump mechanism), or any combination thereof. Additional details of the material supply modules and a number of other features of the printing system can provided in PCT/CN2018/071965, titled "PRECISION PHARMACEUTICAL 3D PRINTING DEVICE" and WO2018210183, titled "3D PRINTING DEVICE AND METHOD," the content of which is incorporated in its entirety.

Figure 1C:
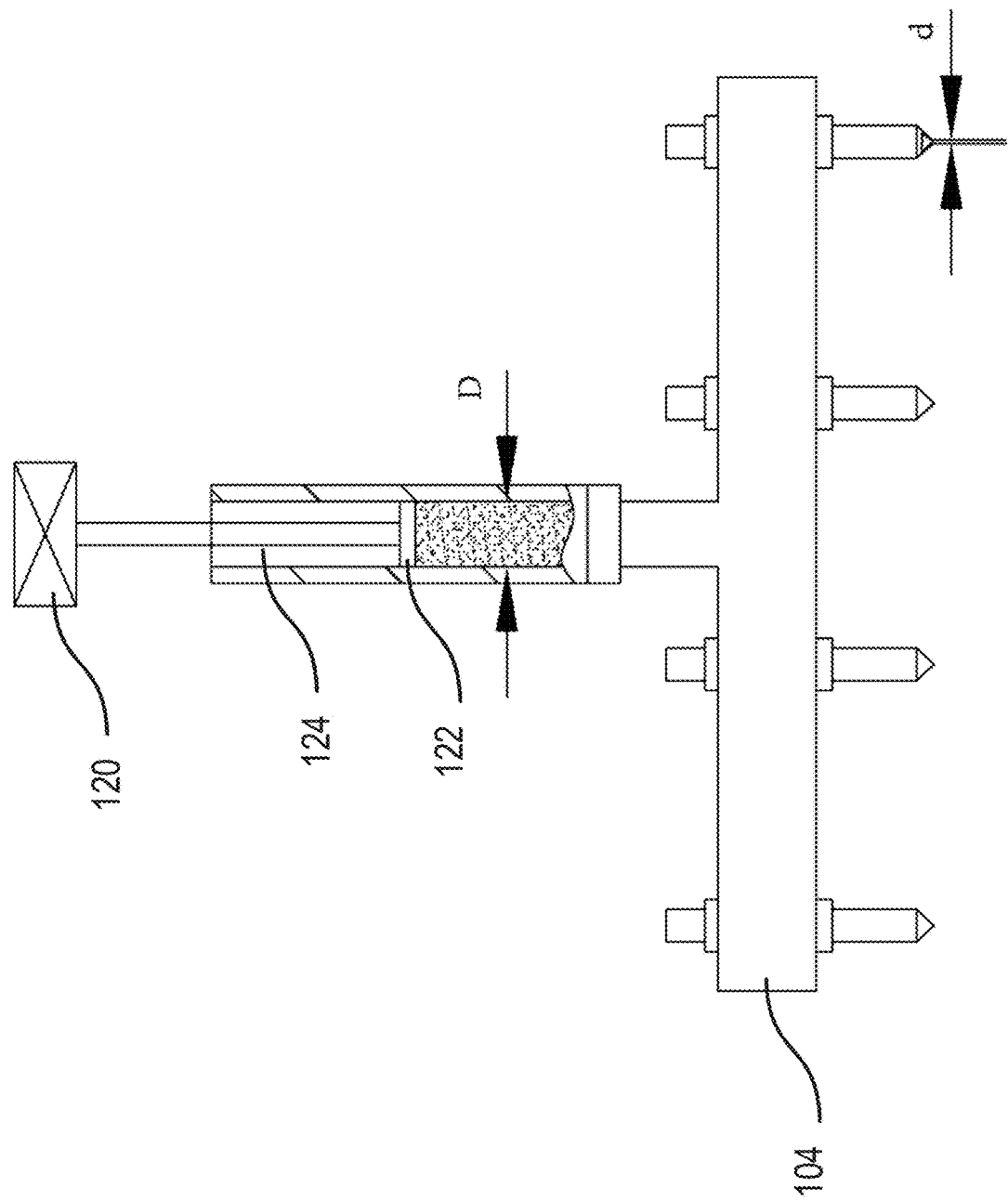
FIG. 1C depicts an exemplary additive manufacturing system comprising a piston mechanism, according to some embodiments of a present invention.

FIG. 1C depicts an exemplary additive manufacturing system comprising a piston mechanism, in accordance with some embodiments of the invention. In the depicted example, a piston 122 is driven by one or more motors 120 in the z direction. When the piston is driven downward, the piston pushes the printing material(s) down the barrel 124, the supply channel 108, and the flow distribution module 104, to alter the pressure of the printing material(s) within the system. Upon opening of the distal outlets of the printing nozzles, the printing material(s) can be dispensed in a precisely controlled manner. The amount of the printing material(s) dispensed can be controlled by controlling the position of the piston, the speed at which the piston moves, the acceleration at which the piston moves, or a combination thereof. In some embodiments, the motor 120 is a stepper motor, server motor, hydraulic control, or a combination thereof.

In some embodiments, the diameter of the barrel, D, is between 5-20 mm. In a preferred embodiment, D is about 10 mm. In some embodiments, the diameter of the nozzle outlet, d, is between 0.1-2 mm. In a preferred embodiment, d is about 0.4 mm. In some embodiments, a ratio parameter, which is indicative of a ratio between the cross-section area of the nozzle outlet and the cross-section area of the barrel is calculated. The ratio can be also expressed as the ratio between $D^2$ squared and $d^2$. In some embodiments, the ratio is calculated as:

$$\frac{D^2}{\sum_{j=1}^{n} d_j^2}$$

Figure 2A:
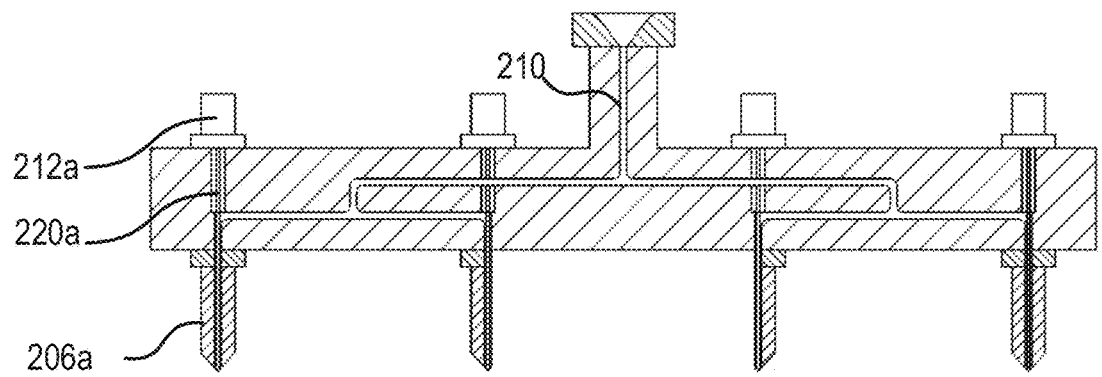
FIG. 2A depicts a side cross-sectional view of an exemplary flow distribution module, according to some embodiments of a present invention.

Turning back to FIG. 1B, the flow distribution module 104 includes a flow distribution plate 114, a plurality of nozzles 106, a temperature control mechanism, pressure sensors, temperature sensors, or any combination thereof. As an example, FIG. 2A depicts a cross-sectional view of an exemplary flow distribution plate. The flow distribution plate comprises a single channel 210 connected to the supply channel of the material supply module for receiving a single flow of printing material(s). The flow distribution plate comprises multiple branched channels configured to divide a single flow into multiple flows, which are dispensed via multiple nozzles, respectively. Each nozzle is configured to dispense a flow of printing material(s) in a controlled manner via a needle-valve mechanism. As depicted, nozzle 206a operates in conjunction with a needle 220a, which is driven by a motor 212a to move in the Z direction. The operation of the needle-valve mechanism is described in more detail below.

Figure 2B:
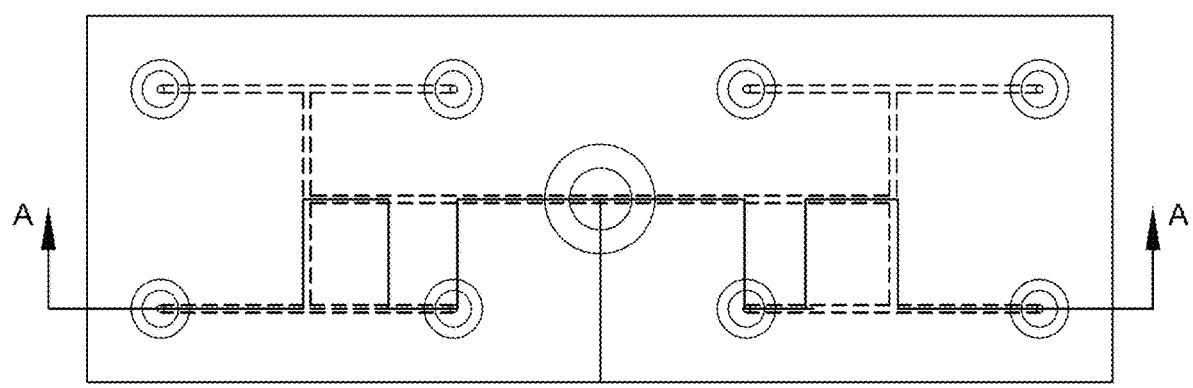
FIG. 2B depicts a top cross-sectional view of an exemplary flow distribution module, according to some embodiments of a present invention.

FIG. 2B depicts a top view of the flow distribution plate shown in FIG. 2A, in accordance with some embodiments. As depicted, the branched channels within the flow distribution plate causes a single flow of printing material(s) to be split into two flows, then into four flows, and then into eight flows. The eight flows of printing material(s) are then dispensed by eight nozzles, respectively.

Figure 2C:
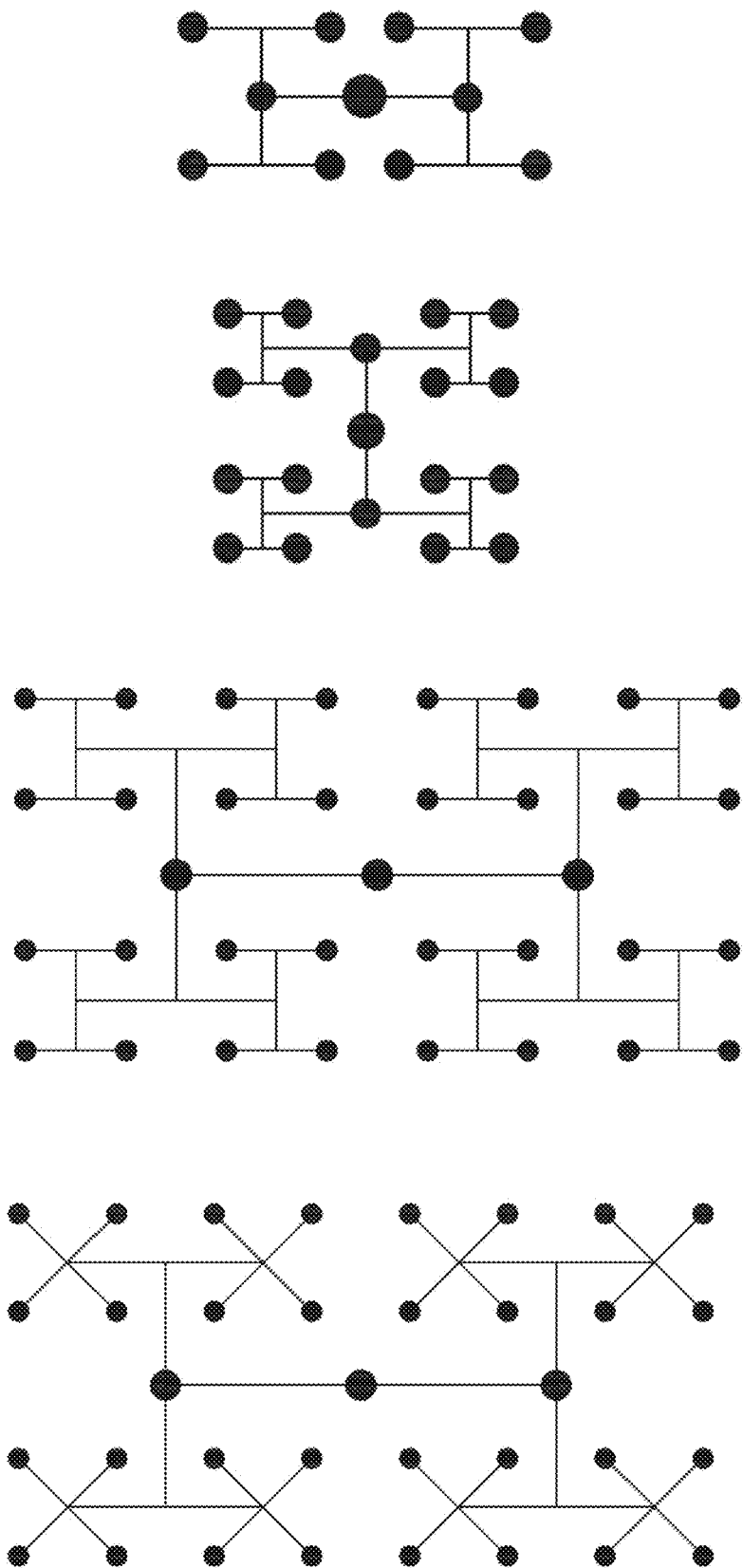
FIG. 2C depicts configurations of an exemplary flow distribution module, according to some embodiments of a present invention.

FIG. 2C depicts exemplary configurations of the channels within a flow distribution plate, in accordance with some embodiments. Each configuration can divide a single flow into multiple flows, which are dispensed at multiple nozzles in an evenly manner (e.g., in terms of weight). Due to the arrangement of channels and junctures within the flow distribution plate, each of the multiple flows traverses a unique flow path which, for example, starts from the top inlet for receiving the single flow from the supply channel into the flow distribution plate and extends to the distal end of the nozzle. In some embodiments, the flow paths of the multiple flows are geometrically symmetrical (e.g., of equal length, of equal geometric shape). In some embodiments, the flow paths of the multiple flows are not geometrically symmetrical, but even distribution is achieved by adjusting the diameters of the flow passage along different portions of the flow path. In some embodiments, some or all of these junctures are positioned over the same or substantially the same plane (e.g., a same X-Y plane). In some embodiments, some or all of these junctures are positioned over different planes (e.g., different X-Y planes).

In some embodiments, the flow distribution plate can be split (e.g., horizontally, vertically, and/or diagonally) into a plurality of components. The plurality of components can be held together by screws. When taken apart, each individual component exposes the inner surfaces of one or more channels and junctures in the flow distribution plate, and thus allows for easier cleaning of the channels and junctures of the flow distribution plate.

In some embodiments, in operation, the pressure within the channels of the flow distribution plate can be between 0-20 MPa (e.g., 0-5 MPa, 0-10 MPa, 0-20 MPa). The amount of time needed for material to traverse the flow distribution plate can be between 5 minutes to 5 hours. In some embodiments, the dispensed volume at a nozzle can be between 0.1-10 µL/s (e.g., 2-3 µL/s).

Turning back to FIG. 1B, the flow distribution plate comprises a temperature control mechanism for maintaining the temperature of the flow distribution plate at a desired level. In some embodiments, the temperature control mechanism comprises one or more heaters and one or more coolers, which are configured to operate in conjunction to maintain the internal temperature of the flow distribution plate.

The one or more heaters can be arranged within the flow distribution plate or in proximity to the flow distribution plate 114. For example, the flow distribution plate comprises internal slots for accommodating one or more heaters (e.g., wires, plates) made of materials of high thermal conductivity. The one or more heating wires extend through the internal slots inside the flow distribution plate 114, for example, as shown in a bottom perspective flow the flow distribution plate in FIG. 2D. The flow distribution plate can comprise multiple rows and columns of internal slots to allow for an even distribution of heating wires throughout the plate such that temperature inside the plate is maintained in a consistent manner.

The one or more coolers can be arranged within the flow distribution plate or in proximity to the flow distribution plate 114. In some embodiments, the temperature control device achieves cooling via water flow. As shown in FIG. 1B, a pair of cooling plates, each having internal channels for running water, are positioned above and below the flow distribution plate 114, thus allowing water flow, air, coolant, etc., to occur in close proximity to the flow distribution plate 114 to regulate the temperature of the plate. In some embodiments, the flow distribution plate comprises internal slots for accommodating one or more coolers within the flow distribution plate. As shown in FIG. 1A, the flow distribution plate 114 and the cooling plates above and below the flow distribution plate 114 are all equipped with inlets 105 for receiving coolant.

Figure 2D:
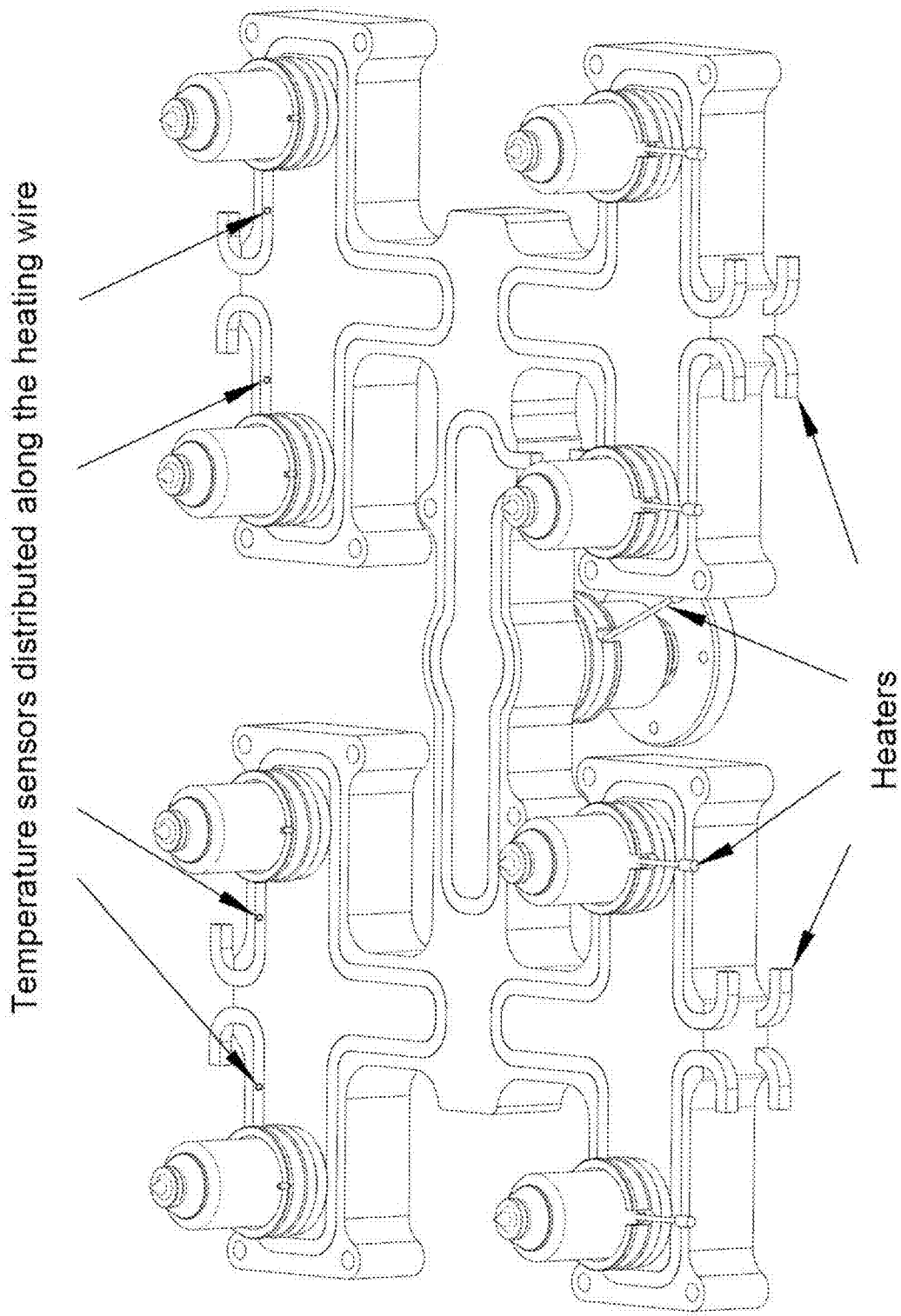
FIG. 2D depicts a bottom perspective view of a flow distribution module, according to some embodiments of a present invention.

In some embodiments, the flow distribution plate comprises one or more temperature sensors connected to a computer system that operates the one or more heaters and coolers in response to a temperature reported by the one or more temperature sensors. FIG. 2D depicts a bottom perspective view of a flow distribution plate and shows an exemplary arrangement of the temperature sensors, in accordance with some embodiments.

In some embodiments, the flow distribution plate comprises one or more pressure sensors 130 configured to detect the pressure of the printing materials within the channels of the flow distribution plate. In some embodiments, the pressure sensors are positioned in proximity to the flow distribution plate (e.g., around the corners, around the peripherals, around the center) or within the channels of the flow distribution plate. In some embodiments, small-range strain-gauge sensors are used.

Figure 3:
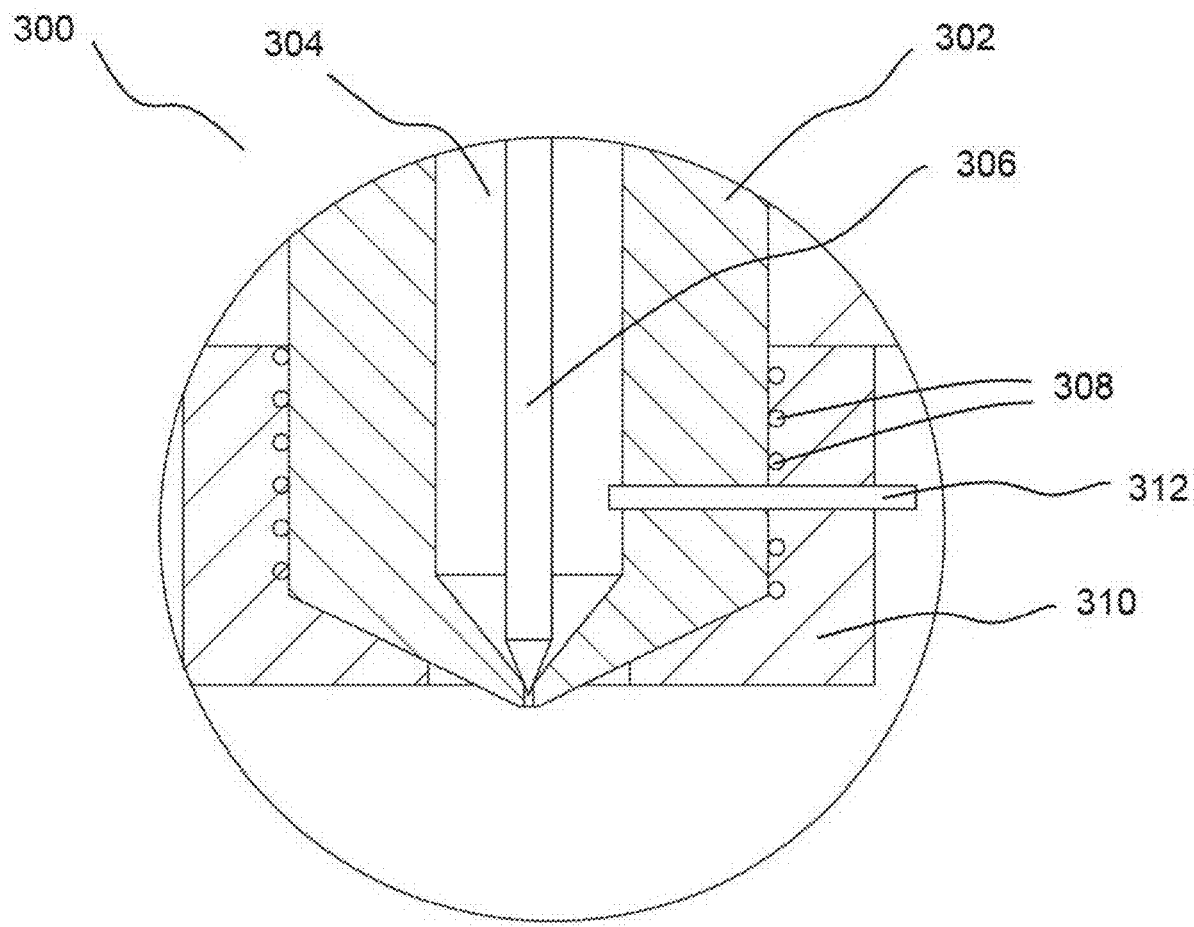
FIG. 3 depicts a cross-sectional view of the distal end of an exemplary nozzle, according to some embodiments of a present invention.

FIG. 3 depicts an exemplary needle-valve mechanism 300 for dispensing printing material at a printing nozzle 302, in accordance with some embodiments. A feed channel 304 is formed along the inside of the nozzle 302 to transport printing material to the distal outlet of the nozzle. The feed channel comprises a chamber that is tapered (e.g., in a cone shape) to serve as the dispensing outlet for the printing material. A sealing needle 306 extends through the feed channel and is driven by a motor system (not depicted) to move along the feed channel. When the needle valve mechanism is in a closed position, the needle is extended such that it is in contact with the tapered distal end of the feed channel and seals the outlet or extrusion port, thus preventing printing material from being dispensed. When the needle is retracted, the outlet is unsealed such that the printing material can be dispensed. To regulate temperature at the distal end of the printing nozzle, the plurality of heating devices 308 and a thermal isolation structure 310 can be placed around the distal end of the nozzle 302. The printing nozzle 302 can further include one or more temperature sensors and/or pressure sensors 312.

In some embodiments, the tapered end of the sealing needle comprises a pointed tip. In some embodiments, the tapered end of the sealing needle is frustoconical. In some embodiments, the tapered inner surface of the feed channel has a first taper angle and the tapered end of the sealing needle has a second taper angle; and wherein the second taper angle is the same or smaller than the first taper angle. In some embodiments, the second taper angle is about 60° or less. In some embodiments, the second taper angle is about 45° or less. In some embodiments, the ratio of the first taper angle to the second taper angle is about 1:1 to about 4:1.

In some embodiments, the extrusion port has a diameter of about 0.1 mm to about 1 mm. In some embodiments, the tapered end has a largest diameter of about 0.2 mm to about 3.0 mm. In some embodiments, the extrusion port has a diameter and the tapered end has a largest diameter, and the ratio of the largest diameter of the tapered end to the diameter of the extrusion port is about 1:0.8 to about 1:0.1.

In some embodiments, the motion system for the needle-valve mechanism comprises: one or more motors, one or more sensors, one or more drivers, and one or more controllers. The sensors can comprise encoders. In some embodiments, the controllers comprises programmable logic controllers ("PLC"). In some embodiments, the divers comprise bus drivers.

In some embodiments, the motion system driving the needles are controlled manually or by a computer controller for regulating the flow at the nozzles. The motion system can comprise a plurality of motors or actuators each coupled to a corresponding needle. The motor may be a mechanical motor (which may comprise a screw), a hydraulic motor, a pneumatic motor (which may comprise a pneumatic valve) or an electromagnetic motor (which may comprise a solenoid valve). Motors that drive the needles can be linear motors, shaft-fixed type motors, non-captive type motors, or a combination thereof.

In some embodiments, a non-captive type linear motor is used in conjunction with anti-backlash nuts and ball spline. Ball spline generally operates with lower friction and thus the motor can operate with higher precision (e.g., ±0.003 mm). Further, the motor is relatively small (e.g., 20-42 mm), thus allowing the spacing between the nozzles to be between 20-50 mm, in some embodiments. Alternatively, a screw linear motor is used.

In some embodiments, each of a plurality of needles is driven by a respective motor. For example, if there are 32 nozzles, there are 32 motors controlling the 32 needles respectively. Further, the motors are each connected to a bus driver (e.g., CAN-open, Modbus).

In some embodiments, the system uses a method of stall detection to find the zero position for the distal end of each needle. During the configuration stage for identifying zero position for a needle, the system configures the corresponding motor to operate at a low electricity level (e.g., 400-1200 mA) and drive the needle toward the distal outlet of the nozzle at a low speed. This is done so that the distal end of the needle would not deform when it is driven against the distal outlet of the nozzle. When the distal end of the needle is in contact with the distal outlet of the nozzle, the needle cannot move further despite the continual driving of the motor. When the encoder no longer detects movement of the needle, the system determines that the needle is at the true zero position. In accordance with the determination that the needle is at the true zero position, the system stops the motor, retracts the needle by 0.003-0.01 mm, and then sets the position of the needle as the configured zero position.

Using the configured zero position ensures that, during the operation of the needle-valve mechanism, the distal end of the needle is not driven against the distal outlet of the nozzle, thus improving the longevity of both the needle and the nozzle. During normal operation, the motor operates at a higher level of electricity (e.g., 1600-1800 mA) and a higher speed (e.g., 0.3-15 mm/s) to ensure swift opening and closing of the valve.

Figure 4:
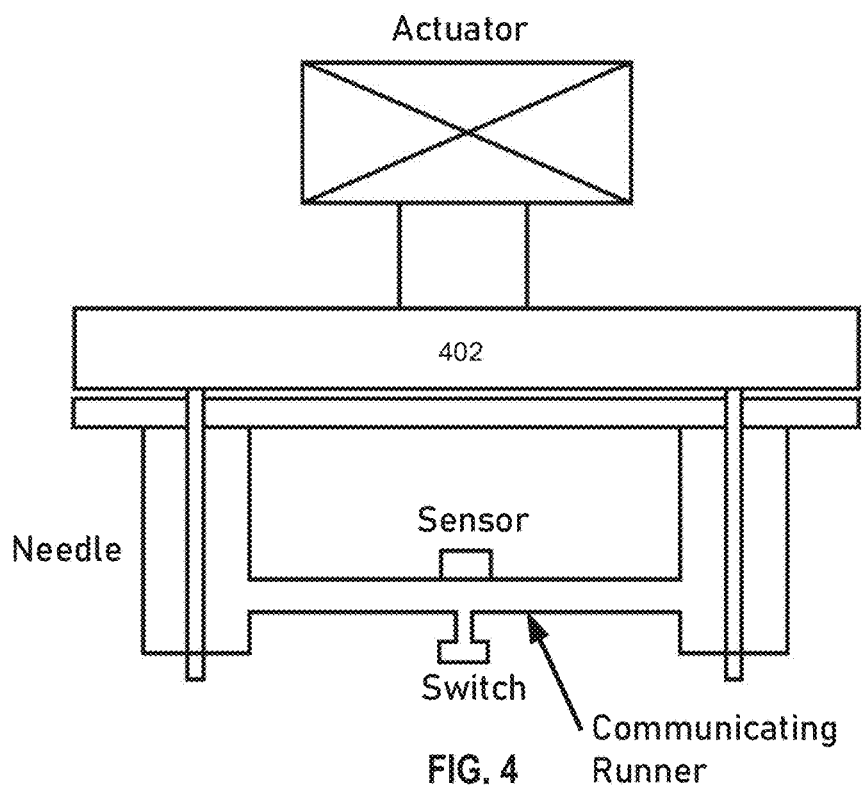
FIG. 4 depicts a cross-sectional view of an exemplary additive manufacturing system, according to some embodiments of a present invention.

In alternative embodiments, the motion system can comprise a single plate coupled to multiple needles such that the retraction of the needles, and thus the dispensing flow of the nozzles are controlled in a uniform manner, as shown in FIG. 4.

In some embodiments, the distal ends of the plurality of nozzles form a plane. In some embodiments, the plane is configured to deviate from the XY plane no more than ±0.01 (±0.005-±0.02). In some embodiments, the plane is configured to have a flatness within ±0.005-±0.02 MM.

The motion system can be activated by a mechanical braking mechanism, a hydraulic braking mechanism, a pneumatic braking mechanism, an electromagnetic braking mechanism, a linear motor, or any combination thereof.

The distal end of the nozzle comprises heaters and insulating materials to maintain the temperature of the distal end. Further, the distal end of the nozzle comprises one or more pressure sensors (see also pressure sensors 132 of FIG. 1B) and temperature sensors, which are configured to directly measure the temperature and pressure of the printing material inside the nozzle. In some embodiments, the one or more pressure sensors include small-range strain-gauge sensors.

In some embodiments, the diameter of the channels within the flow distribution plate is between 1-16 mm. In some embodiments, the diameter of the feed channel within the nozzle is between 0.1-1.0 mm. In some embodiments, the diameter of the needle is between 0.1-6 mm. In some embodiments, the diameter of the distal outlet of the nozzle is between 0.05-3.0 mm. In some embodiments, the spacing between each nozzle is between 8-50 mm. In a preferred embodiment, the spacing between two nozzles is between 20-50 mm, and the diameter of the outlet of a nozzle is between 0.05-0.8 or between 0.8-1.0 mm.

In some embodiments, the system comprises a plurality of needle-valve mechanisms, a push plate, a flow distribution plate, and a needle-valve adjustment system. The needle-valve adjustment system comprises a first elastic component, a second elastic component, a push-plate actuator, and a locking mechanism, as described below. The needle-valve adjustment system allows the amount of opening of each needle-valve mechanism to be adjusted in a precise manner such that the needle-valve mechanisms all operate (e.g., dispense printing material) uniformly. The push plate allows all needle-valve mechanisms to open/close simultaneously.

The proximal end of the needle can be coupled to a push plate such that vertical movement of the push plate can cause vertical movement of the needle. In some embodiments, multiple needles are coupled to the same push plate such that the movement of the push plate can cause multiple needles to move simultaneously. The push plate can be driven using any motion system, such as a wedge mechanism, a cam mechanism, etc. In some embodiments, the push plate is placed above the flow distribution plate.

In some embodiments, the hub of the needle at the proximal end of the needle is housed within a sleeve component. The sleeve component comprises an upper ceiling and a lower floor. The lower floor comprises a hole that is large enough to allow the stem portion of the needle to pass through but small enough to retain the hub of the needle within the sleeve. A first elastic component can be disposed above the hub of the needle and is sandwiched between the hub of the needle and the upper ceiling of the sleeve component. In some embodiments, the first elastic component is a coil. Thus, the first elastic component can push the hub of the needle downward such that the hub is in contact with the lower floor of the sleeve.

In operation, when the push plate travels downward to close the needle valve, the first elastic component can be retracted such that the hub of the needle has room to move upward within the sleeve, thus creating a buffering effect and reducing the force on the distal tip of the needle as it comes into contact with the nozzle. When multiple needles are coupled to the push plate and each needle has a corresponding sleeve, this mechanism allows all needles to close the corresponding nozzles in a uniform manner.

In some embodiments, the push plate comprises a recess on the upper surface of the push plate. Further, at least the lower portion of the sleeve can be disposed within the recess. The upper portion of the sleeve can be coupled to a support structure via a locking mechanism, and the support structure is affixed to the push plate. In some embodiments, the locking mechanism comprises a horizontal plate with a hole, which allows the sleeve to pass through. The locking mechanism can be adjusted (e.g., the size of the hole can be adjusted) such that the sleeve can be clamped via the hole. Thus, the sleeve can be affixed to the push plate (i.e., via the locking mechanism and the support) such that the sleeve does not move relative to the push plate during printing. In some embodiments, a second elastic component is placed within the recess below the sleeve. For example, the second elastic component can be a coil sandwiched between the bottom of the recess and the bottom of the sleeve.

During the initialization stage, the vertical position of the sleeves can be manually or automatically adjusted to adjust the vertical position of the needles. For example, the vertical position of the sleeve can be adjusted depending on where the sleeve is clamped by the locking mechanism. By adjusting the vertical position of the sleeves and thus the needles, the amount of opening at the nozzles can be adjusted accordingly. The adjustment can be done during the initialization stage to ensure that the needles can be controlled in a uniform manner (e.g., same travel displacement) to dispense the same amount of printing material during printing.

In some embodiments, the motion system that drives the push plate includes an actuator. In some embodiments, the actuator is disposed over the sleeve component(s). The actuator can be a pneumatic actuator, a mechanical actuator, an electromagnetic actuator, hydraulic actuator, or an electrical motor. The motion system can be coupled to the push plate, for example, via the support structure described above.

With reference to FIG. 4, the system comprises a communicating runner connecting two nozzles. The pressure at the two nozzles can be automatically balanced and controlled via a close-loop flow control system that includes a sensor and a motor. A switch is added to allow printing materials in the communicating runners to be periodically dispensed to prevent the printing materials from being held in the runner for an extended period of time and breaking down in the runner. In some embodiments, multiple sets of communicating runners can be provided to connect multiple nozzles. Further, both needles are coupled to a single plate such that the movement of the plate 402 (e.g., via manual control, via a motor) causes the needles to move in a uniform manner.

Turing back to FIG. 1A, printing platform 110 is arranged on a stage-driving mechanism. The stage-driving mechanism may drive the printing platform 110 relative to the movement of the nozzles 106. In some embodiments, the stage-driving mechanism may be a stepper motor, linear motor, or servo motor based on the Cartesian coordinate system so that it can drive printing platform 110 along the X-axis, one direction of the Y and Z axes or more direction. In other embodiments, the printing apparatus 100 further includes a module drive mechanism for driving movement of the printing platform module 110 with respect to the nozzle 106. In still other embodiments, the stage-driving mechanism may be a transfer track. With the printing platform 110 and the relative movement of the nozzles 106, the printing material is deposited into complex structures and the desired configuration on the printing platform 110. It should be appreciated that other coordinate systems and/or movement can be used.

In some embodiments, multiple arrays of nozzles are used to print a single batch of pharmaceutical dosage units. For example, a first array of nozzles is configured to dispense a first type of printing material, while a second array of nozzles is configured to dispense a second type of printing materials. By switching among multiple arrays of nozzles, each resulting tablet can comprise layers of different materials. As discussed, each nozzle comprises a needle valve mechanism, which is coupled to a corresponding motor 112 and a computer controller for controlling the output of printing material such that the resulting pharmaceutical dosage units are consistent in the same batch and across multiple batches in volume, weight, and/or composition.

Figure 1D:
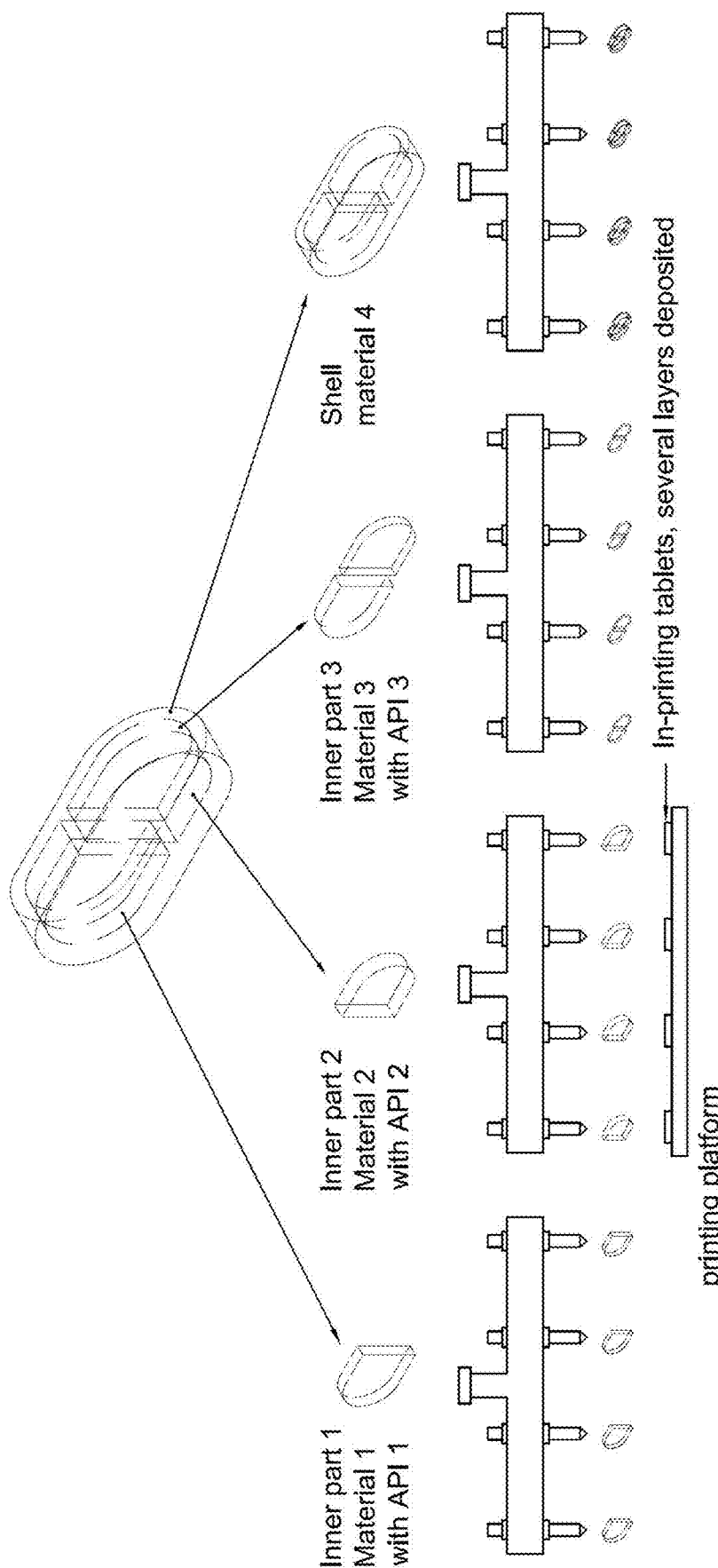
FIG. 1D depicts an exemplary additive manufacturing system, according to some embodiments of a present invention.

FIG. 1D depicts an exemplary system for printing pharmaceutical dosage units using multiple arrays of nozzles, in accordance with some embodiments. In the depicted example, the pharmaceutical dosage unit to be printed comprises four parts: Inner Part 1, Inner Part 2, Inner Part 3, and a Shell. The printing process occurs in four phases. In the first phase, a first array of nozzles are configured to dispense Material 1 based on a first set of instructions to print a batch of Inner Part 1 units. In some embodiments, the set of instructions is implemented as an API. In the second phase, a second array of nozzles are configured to dispense Material 2 based on API 2 to print a batch of Inner Part 2 units. In the third phase, a third array of nozzles are configured to dispense Material 3 based on API 3 to print a batch of Inner Part 3 units. In the first, second, and third phases, the batches of parts are all printed over the same printing platform. Further, each Inner Part 1 unit has a corresponding Inner Part 2 unit and Inner Part 3 unit, and the three units are generated on the printing platform such that the relative placement of the three units is consistent with the desired placement within a pharmaceutical dosage unit.

In the fourth phase, a fourth array of nozzles are configured to dispense Material 4 based on API 4 to print a batch of shells. Each shell is created to coat over an Inner Part 1 unit and the corresponding Inner Part 2 unit and the Inner Part 3 unit to form a final pharmaceutical unit.

The printing material comprises viscous materials. In some embodiments, it is medicinal material or thermoplastic material, or a combination thereof. In some embodiments, the material is dispensed from a nozzle at a temperature of about 25 degrees to about 400 degrees Celsius. In some embodiment, the viscosity of the material is between 0.001-10000 Pa·s.

In some embodiments, the material is a non-filamentous material, such as a powder, granules, a gel, or a paste. The non-filamentous material is melted and pressurized so that it can be dispensed through an extrusion port of a nozzle. As described further herein, pressure of particularly viscous materials is carefully controlled to ensure precise and accurate depositing of the material. The material can be melted within the material supply module using one or more heaters disposed within the material supply module, such as within or surrounding a barrel containing the material, a feed channel, and/or a nozzle. In some embodiments, the melting temperature of the material is about 30° C. or higher, such as about 60° C. or higher, about 70° C. or higher, about 80° C. or higher, about 100° C. or higher, about 120° C. or higher, about 150° C. or higher, about 200° C. or higher, or about 250° C. or higher. In some embodiments, the melting temperature of the material is about 400° C. or lower, such as about 350° C. or lower, about 300° C. or lower, about 260° C. or lower, about 200° C. or lower, about 150° C. or lower, about 100° C. or lower, or about 80° C. or lower. Material dispensed from the nozzle can be dispensed at a temperature at or above the melting temperature of the material. In some embodiments, the material is dispensed at a temperature of about 50° C. or higher, such as about 60° C. or higher, about 70° C. or higher, about 80° C. or higher, about 100° C. or higher, about 120° C. or higher, about 150° C. or higher, about 200° C. or higher, or about 250° C. or higher. In some embodiments, the material is dispensed at a temperature of about 400° C. or lower, such as about 350° C. or lower, about 300° C. or lower, about 260° C. or lower, about 200° C. or lower, about 150° C. or lower, about 100° C. or lower, or about 80° C. or lower.

The system described herein is useful for accurately and precisely dispensing viscous materials. In some embodiments, the material has a viscosity of about 100 Pa·s or more, such as about 200 Pa·s or more, about 300 Pa·s or more, about 400 Pa·s or more, about 500 Pa·s or more, about 750 Pa·s or more, or about 1000 Pa·s or more, when dispensed from the device. In some embodiments, the material has a viscosity of about 2000 Pa·s or less, such as about 1000 Pa·s or less, about 750 Pa·s or less, about 500 Pa·s or less, about 400 Pa·s or less, about 300 Pa·s or less, or about 200 Pa·s or less.

In some embodiments, the material is a pharmaceutically acceptable material. In some embodiments, the material is inert or biologically inert. In some embodiments, the material is an erodible material or a bioerodible material. In some embodiments, the material is a non-erodible material or a non-bioerodible material. In some embodiments, the material is a pharmaceutically acceptable material. In some embodiments, the material comprises one or more thermoplastic materials, one or more non-thermoplastic material, or a combination of one or more thermoplastic materials and one or more non-thermoplastic materials. In some embodiments, the material is a polymer or a co-polymer.

In some embodiments, the material comprises a thermoplastic material. In some embodiments, the material is a thermoplastic material. In some embodiments, the material is or comprises an erodible thermoplastic material. In some embodiments, the thermoplastic material is edible (i.e., suitable for consumption by an individual). In some embodiments, the thermoplastic material is selected from the group consisting of a hydrophilic polymer, a hydrophobic polymer, a swellable polymer, a non-swellable polymer, a porous polymer, a non-porous polymer, an erodible polymer (such as a dissolvable polymer), a pH sensitive polymer, a natural polymer, a wax-like material, and a combination thereof. In some embodiments, the thermoplastic material is a cellulose ether, a cellulose ester, an acrylic resin, ethylcellulose, hydroxypropylmethylcellulose, hydroxypropyl cellulose, hydroxymethylcellulose, a mono- or diglyceride of $C_{12}$-$C_{30}$ fatty acid, a $C_{12}$-$C_{30}$ fatty alcohol, a wax, poly(meth)acrylic acid, polyvinyl caprolactam-polyvinyl acetate-polyethylene glycol graft copolymer 57/30/13, polyvinylpyrrolidone-co-vinyl-acetate (PVP-VA), polyvinylpyrrolidone-polyvinyl acetate copolymer (PVP-VA) 60/40, polyvinylpyrrolidone (PVP), polyvinyl acetate (PVAc) and polyvinylpyrrolidone (PVP) 80/20, vinylpyrrolidone-vinyl acetate copolymer (VA64), polyethylene glycol-polyvinyl alcohol graft copolymer 25/75, kollicoat IR-polyvinyl alcohol 60/40, polyvinyl alcohol (PVA or PV-OH), poly(vinyl acetate) (PVAc), poly(butyl methacrylate-co-(2-dimethylaminoethyl) methacrylate-co-methyl methacrylate) 1:2:1, poly(dimethylaminoethylmethacrylate-co-methacrylic esters), poly(ethyl acrylate-co-methyl methacrylate-co-trimethylammonioethyl methacrylate chloride), poly(methyl acrylate-co-methyl methacrylate-co-methacrylic acid) 7:3:1, poly(methacrylic acid-co-methylmethacrylate) 1:2, poly(methacylic acid-co-ethyl acrylate) 1:1, poly(methacylic acid-co-methyl methacrylate) 1:1, poly(ethylene oxide) (PEO), poly(ethylene glycol) (PEG), hyperbranched polyesteramide, hydroxypropyl methylcellulose phthalate, hypromellose phthalate, hydroxypropyl methylcellulose or hypromellose (HMPC), hydroxypropyl methylcellulose acetate succinate or hypromellose acetate succinate (HPMCAS), poly(lactide-co-glycolide) (PLGA), carbomer, poly(ethylene-co-vinyl acetate), ethylene-vinyl acetate copolymer, polyethylene (PE), and polycaprolactone (PCL), hydroxyl propyl cellulose (HPC), polyoxyl 40 hydrogenerated castor oil, methyl cellulose (MC), ethyl cellulose (EC), poloxamer, hydroxypropyl methylcellulose phthalate (HPMCP), poloxamer, hydrogenated castor oil, hydrogenated soybean oil, glyceryl palmitostearate, carnauba wax, polylactic acid (PLA), polyglycolic acid (PGA), cellulose acetate butyrate (CAB), polyvinyl acetate phthalate (PVAP), a wax, beeswax, hydrogel, gelatin, hydrogenated vegetable oil, polyvinyl acetal diethyl aminolactate (AEA), paraffin, shellac, sodium alginate, cellulose acetate phthalate (CAP), arabic gum, xanthan gum, glyceryl monostearate, octadecanoic acid, thermoplastic startch, derivatives thereof (such as the salts, amides, or esters thereof), or a combination thereof.

In some embodiments, the erodible material comprises a non-thermoplastic material. In some embodiments, the erodible material is a non-thermoplastic material. In some embodiments, the non-thermoplastic material is a non-thermoplastic starch, sodium starch glycolate (CMS-Na), sucrose, dextrin, lactose, microcrystalline cellulose (MCC), mannitol, magnesium stearate (MS), powdered silica gel, titanium dioxide, glycerin, syrup, lecithin, soybean oil, tea oil, ethanol, propylene glycol, glycerol, Tween, an animal fat, a silicone oil, cacao butter, fatty acid glycerides, vaseline, chitosan, cetyl alcohol, stearyl alcohol, polymethacrylate, non-toxic polyvinyl chloride, polyethylene, ethylene-vinyl acetate copolymer, silicone rubber, or a combination thereof.

Exemplary materials that may be used with the device described herein or the methods described herein include, but are not limited to, a poly(meth)acrylate co-polymer (such as a co-polymer containing one or more of amino alkyl methacrylate, methacrylic acid, metacrylic ester, and/or ammonioalkyl methacrylate, such as a copolymer sold under the brand name Eudragit® RSPO) and hydroxyl propyl cellulose (HPC). In some embodiments, the material comprises a drug. In some embodiments, the material is admixed with a drug.

Figure 6A:
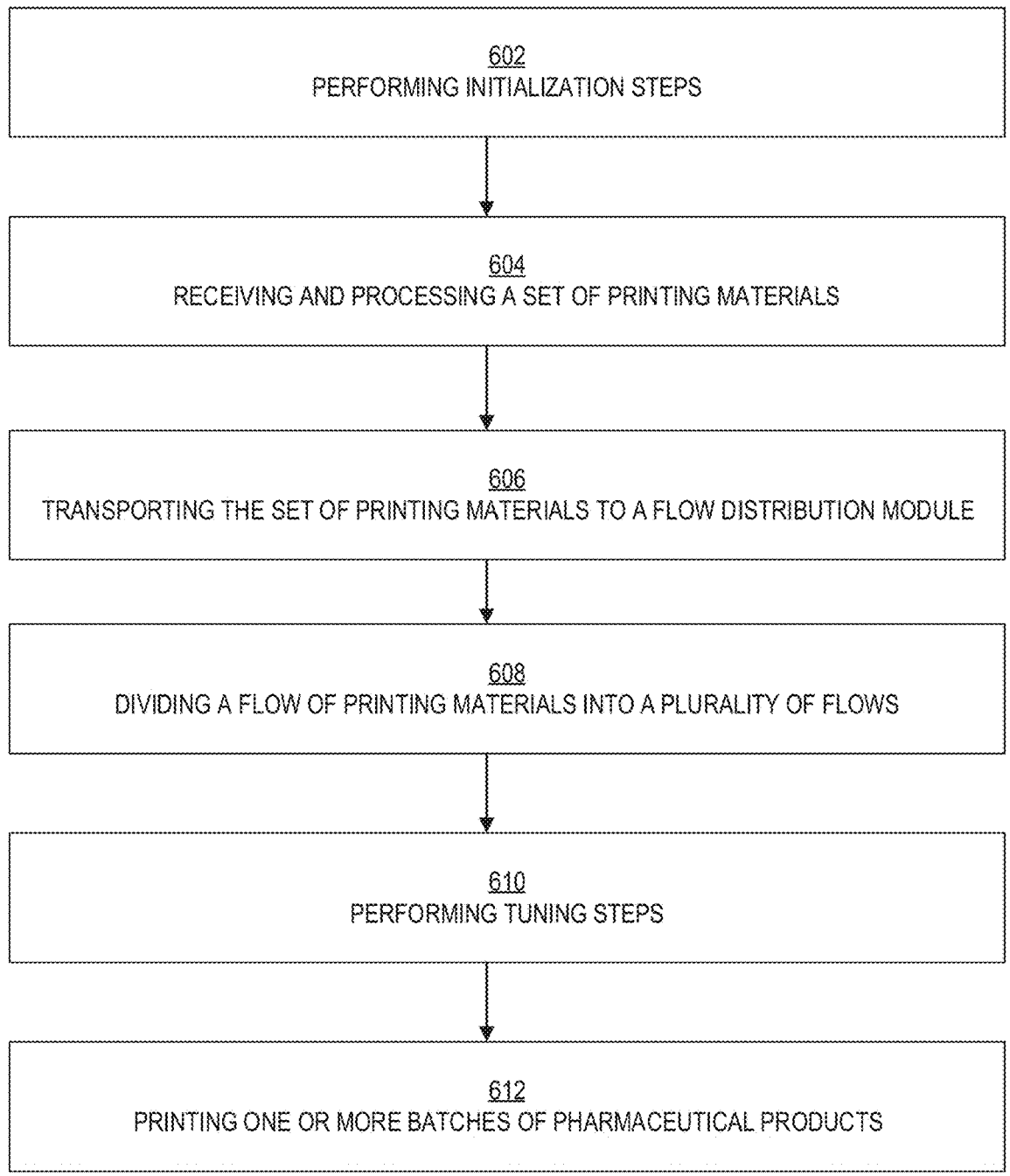
FIG. 6A depicts an exemplary process for 3D printing pharmaceutical dosage units, according to some embodiments of a present invention.

FIG. 6A depicts an exemplary process 600 for 3D printing pharmaceutical dosage units, according to some embodiments of a present invention. Process 600 is performed, for example, using a printing system 100. In process 600, some blocks are, optionally, combined, the order of some blocks is, optionally, changed, and some blocks are, optionally, omitted. In some examples, additional steps may be performed in combination with the process 600. Accordingly, the operations as illustrated (and described in greater detail below) are exemplary by nature and, as such, should not be viewed as limiting.

In some embodiments, the printing system comprises one or more computer controllers. The computer controllers can be programmed based on a plurality of manufacturing parameters. The plurality of manufacturing parameters include printing speed, target temperature values associated with different portions of the printing system (e.g., the flow distribution plate, the distal end of the nozzles, the material supply module, the pump), and pressure curves. In some embodiments, some of the manufacturing parameters are specified by the user, while others are automatically calculated by a computer. The manufacturing parameters can be determined based on desired metrics of the pharmaceutical dosage units (e.g., volume, weight, composition, dimensions), the printing materials, and/or the settings of the printing system. In some embodiments, programming logic/code is generated based on the plurality of manufacturing parameters.

At block 602, the printing system performs initialization steps. The initialization steps can include starting up the system, loading necessary data (e.g., 3D models) and programming logic, initialize parameters, or a combination thereof. The initialization steps can further comprises a heating process to achieve desired temperatures at various components of the printing system (e.g., raising the temperature of the heating wires). In some embodiments, the heating process is controlled by a proportional-integral-derivative controller ("PID controller"). Specifically, the PID controller can measure (e.g., periodically) temperatures of various components of the printing system and determine whether one or more target temperatures are realized. In accordance with a determination that the one or more target temperatures are not realized, the PID controller continues the heating process. In accordance with a determination that the one or more target temperatures are realized, the PID controller provides an output. In some embodiments, the output is a visual, audible, or haptic output to alert a human worker to add printing materials. In some embodiments, the output is an output signal that triggers the printing materials to be added to the printing system automatically.

At block 604, the system receives and processes a set of printing materials. The printing materials can include active ingredients and/or excipients in a predefined composition. The printing materials can include medicinal material, thermoplastic material, and a combination thereof. At the material supply module, the printing materials are blended, plasticized, and melted. At block 606, the processed printing materials are transported as a single flow to the flow distribution module, for example, via a single screw pump (e.g., gear pump or screw valve).

At block 608, the flow distribution module divides the single flow of processed printing materials into a plurality of flows. Specifically, the flow distribution plate comprises a plurality of channels such as those described with reference to FIGS. 2A-C. Through the channels, the plurality of flows reach the distal ends of a plurality of nozzles. When the printing system starts up, the needle-valve mechanisms of the nozzles are in closed position, thus preventing the plurality of flows from being dispensed. In some embodiments, the needle-value mechanisms of the nozzles are not activated until a desired temperature is reached at the nozzles.

At block 610, the system performs tuning steps. FIG. 5B depicts an exemplary process 550 for tuning the 3D printing system, in accordance with some embodiments.

At block 652, the system starts dispensing the plurality of flows at the plurality of nozzles to produce a first batch of test pharmaceutical dosage units (e.g., tablets caplets, printlets). Specifically, as each flow of printing materials accumulates at the sealed distal end of the corresponding nozzle, the pressure sensors (e.g., at the distal end of the nozzle, at the flow distribution plate) start receiving higher pressure readings. When the pressure readings exceed a predefined threshold, the needle-valve mechanisms may be opened to start dispensing the plurality of flows. Before the needle-valve mechanisms are opened, the system maintains the pressure of the printing materials at the nozzles. The opening of the needle-valve mechanisms can be triggered by one or more controllers at any time.

Figure 5:
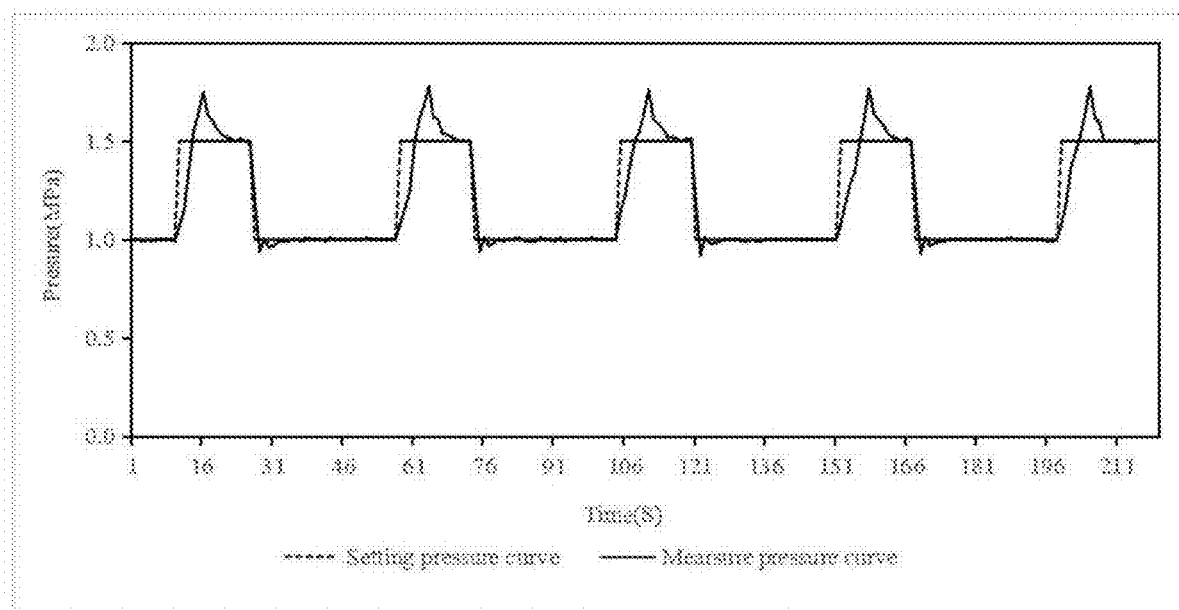
FIG. 5 depicts an exemplary pressure curve for dispensing printing material at a nozzle, according to some embodiments of a present invention.

Upon opening of the needle-valve mechanisms, the system starts dispensing the plurality of flows to 3D print the first batch of plurality of test pharmaceutical dosage units (e.g., tablets caplets, printlets). The flow volume for 3D printing a single batch of units is controlled via a closed-loop control system based on a predefined pressure curve. FIG. 5 illustrates an exemplary pressure curve, in which each cycle represents a session of opening, printing, and closing of the needle-valve mechanism.

At blocks 654-662, the system makes iterative adjustments to nozzles and the material supply module until the sum of weights of a test batch (e.g., a batch of 32 tablets) falls within a predefined margin of error, while improving the consistency among the weights of a test batch (e.g., the consistency among the weights of 32 tablets). At block 554, the system determines whether a sum of weights of the test batch differs from a target total weight by a predefined amount (e.g., +/−0.5%, +/−1%, +/−2%, +/−3%, +/−4%, +/−5%).

At block 656, in accordance with a determination that the error difference is higher than the predefined amount, the system makes adjustments to reduce error. In some embodiments, block 556 includes adjusting one or more nozzles (block 558) and adjusting the material supply module (block 560).

At block 658, the system adjusts one or more nozzles, specifically the openings at the one or more nozzles, based on an average weight of the batch of test units. The goal is to reduce the variance among the outputs of the nozzles. For each nozzle, the adjustment is determined based on the formula below.

$$H_{next} = H_C - \alpha^*(W_A - W_C) \quad (1)$$

In the formula above, $H_{next}$ represents the amount of opening of the needle-valve mechanism of the respective nozzle in the next iteration (in millimeter); $H_c$ represents the amount of opening of the needle-valve mechanism of the respective nozzle in the current iteration (in millimeter); $W_A$ represents the average weight of the test batch in the current iteration (in milligram); $W_C$ represents the weight of the test unit produced by the respective nozzle in the current iteration (in milligram); a represents an opening coefficient, which can vary for different needle-valve mechanisms (in mm/mg). In some embodiments, a machine learning algorithm can be used to determine the amount of opening at each nozzle. The amount of opening of the needle-valve is directed related to the travel displacement of the needle—as the needle travels upward, the amount of opening increases; as the needle travels downward, the amount of opening decreases. The terms "amount of opening" and "travel displacement" are used interchangeable herein.

At block 660, the system adjusts the material supply module, for example, by adjusting the pressure and temperature (e.g., based on the pressure readings at the nozzles, based on the pressure readings at the flow distribution plate), adjusting the feeding speed/amount, or any combination thereof. For example, if the total weight of the test batch exceeds the target batch weight, the system can reduce the pressure, reduce the temperature, reduce feeding speed/amount, or any combination thereof.

At block 662, after the adjustments are made, the system opens the needle-valve mechanisms to 3D print another batch of plurality of test units. At block 554, the system determines whether a sum of weights of the new test batch differs from a target total weight by a predefined amount (e.g., +/−0.5%, +/−1%, +/−2%, +/−3%, +/−4%, +/−5%). If not, the system repeats the steps in 556 to continue adjusting the material supply modules and the nozzles.

At block 664, in accordance with a determination that the sum of weights of the new test batch does not differ from a target total weight by the predefined amount, the system adjusts one or more nozzles based on a target weight of the pharmaceutical unit. In other words, after achieving a target batch weight while improving the consistency among the nozzle outputs, the system then makes adjustments to the nozzles to make sure each nozzle can achieve the target weight (e.g., a target weight of a particular tablet).

Specifically, the system adjusts one or more nozzles, specifically the openings at the one or more nozzles, based on a target weight of the pharmaceutical unit. For each nozzle, the adjustment is determined based on the formula below.

$$H_{next} = H_C - \alpha^*(W_T - W_C) \quad (2)$$

In the formula above, $H_{next}$ represents the amount of opening of the needle-valve mechanism of the respective nozzle in the next iteration (in millimeter); $H_c$ represents the amount of opening of the needle-valve mechanism of the respective nozzle in the current iteration (in millimeter); $W_T$ represents the target weight of the unit (in milligram); $W_C$ represents the weight of the test unit produced by the respective nozzle in the current iteration (in milligram); a represents an opening coefficient, which can vary for different needle-valve mechanisms (in mm/mg). In some embodiments, a machine learning algorithm can be used to determine the amount of opening at each nozzle.

The primary difference between formula (1) and (2) is the difference between $W_T$ and $W_A$. In some embodiments, the batch weight is first adjusted, for example, by adjusting pressure and temperature within the system. When the batch weight is within a desirable range, the unit weight is adjusted, for example, by adjusting the opening and closing of the needle valves.

At block 666, the system 3D prints a new test batch. At block 668, the system determines whether the weight of each test unit in the new test batch differs from the target unit weight by a predefined amount (e.g., +/−0.5%, +/−1%, +/−2%, +/−3%, +/−4%, +/−5%). In some embodiments, the predefined amount is +/−1.5%. If no, the initialization is complete. If yes, the system continues the tuning steps by repeated some or all of steps 654-664.

The tuning steps described above are exemplary. Parameters other than weight of a pharmaceutical unit, such as weight of output deposit (e.g., extruded wire), volume, dimension, and/or composition, can be used in the tuning steps to achieve consistency among the nozzles and across batches in these parameters.

The tuning steps can be used in conjunction with close-loop control systems. In some embodiments, the system comprises a temperature close-loop control system, which adjusts the heater and the temperature control device based on temperature readings (e.g., from temperature sensors in the material supply module, the flow distribution plate, or nozzle) to achieve and maintain the target temperature. In some embodiments, average of temperature readings from multipole temperature sensors is used. For example, a temperature sensor can transmit a measured temperature to a computer system, and the computer system can operate the one or more heaters to ensure an approximately constant temperature. The temperature sensor in the nozzle can operate with the one or more heaters in the nozzle in a closed-loop feedback system to ensure approximately constant temperature of the material within the nozzle.

The temperature sensors described herein can comprise thermocouple sensors (e.g., type J, type K) or resistance thermometers. In some embodiments, the temperature sensors are configured to measure temperature below 200° C. The pressure sensors described herein comprise piezo-resistance type transducers or strain-gauge sensors. In some embodiments, small-range strain-gauge sensors are used. Depending on the location of the temperature or pressure sensor (e.g., within or in proximity to the material supply module, flow distribution plate, or nozzle), different types of the sensor can be used.

In some embodiments, the one or more heaters in the system heat the material within the system to a temperature at or above the melting temperature of the material. In some embodiments, the one or more heaters heats the material to a temperature of about 60° C. or higher, such as about 70° C. or higher, 80° C. or higher, 100° C. or higher, 120° C. or higher, 150° C. or higher, 200° C. or higher, or 250° C. or higher. In some embodiments, the one or more heaters heats the material to a temperature of about 300° C. or lower, such as about 260° C. or lower, 200° C. or lower, 150° C. or lower, 100° C. or lower, or 80° C. or lower. In some embodiments, the one or more heaters heat the material to different temperatures at different locations of the device. For example, in some embodiments, the material is heated to a first temperature within the barrel, a second temperature within the feed channel, and a third temperature within the nozzle, each of which may the same temperature or different temperatures. In some embodiments, the temperature of the material at the nozzle is higher than the feed channel and the channels in the flow distribution plate, for example, by 0-10° C. or 0-20° C. By way of example, a material may be heated to 140° C. in the barrel and the feed channel, but to 160° C. when in the nozzle. The feedback control system allows high precision of the temperature. In some embodiments, the temperature is controlled within 0.1° C. of the target temperature, within 0.2° C. of the target temperature, within 0.5° C. of the target temperature, within 1° C. of the target temperature, or within 10° C. of the target temperature.

In some embodiments, the system comprises a pressure close-loop control system, which adjusts the material supply module (e.g., the rotation speed of the screw mechanism) based on pressure readings (e.g., from pressure sensors in the flow distribution plate or nozzle) to achieve and maintain the target pressure. In some embodiments, average of pressure readings from multipole pressure sensors is used.

In some embodiments, the pressure sensors are configured to detect pressure of the material within the nozzle or the feed channel proximal to the nozzle. In some embodiments, pressure sensors are positioned within the nozzle or adjacent to the feed channel and proximal to the nozzle. The pressure sensors can operate with the pressure controller in a closed-loop feedback system to provide approximately constant pressure to the material in the device. For example, when a pressure sensor detects a decrease in pressure, feedback system can signal the pressure controller to increase pressure of the material (e.g., by lowering the piston, increasing air pressure in the barrel, turning the pressure screw, etc.). Similarly, when the pressure sensor detects an increase in pressure, the feedback system can signal the pressure controller to decrease pressure of the material (e.g., by raising the piston, decreasing air pressure in the barrel, turning the pressure screw, etc.). Constant pressure ensures that the melted material in the device is dispensed through the extrusion port of the nozzle at a constant rate when the sealing needle is in the open position. However, when the sealing needle is in a closed position, constant pressure increase (e.g., by raising the piston, decreasing air pressure in the barrel, turning the pressure screw, etc.) may cause leakage of the melted material through the nozzle. Additionally, the feedback system including the pressure sensor and pressure controller keeps an approximately constant pressure in the system when the sealing needle is repositioned from the open position to the closed position, or from the closed position to the open position. This minimizes a "ramp up" in extrusion rate when the sealing needle is positioned in the open position from the closed position because there is no need to ramp up pressure of the material in the system. The feedback system can be operated using a proportional-integral-derivative (PID) controller, a bang-bang controller, a predictive controller, a fuzzy control system, an expert system controller, or any other suitable algorithm. In some embodiments, the sample rate of the pressure sensor is about 20 ms or less, such as about 10 ms or less, about 5 ms or less, or about 2 ms or less. In some embodiments, the pressure is controlled within 0.01 MPa of the target pressure, within 0.05 MPa of the target pressure, within 0.1 MPa of the target pressure, within 0.2 MPa of the target pressure, within 0.5 MPa of the target pressure, or within 1 MPa of the target pressure.

Turning back to FIG. 6A, at block 612, the system prints one or more batches of pharmaceutical dosage units. In some embodiments, the system periodically conducts quality checks on the pharmaceutical dosage units, for example, by measuring the batch weights or the unit weights and determining whether they are within desirable ranges. If the batch weights or the unit weights fall out of the desirable ranges, the system can perform some or all of steps 654-664 to make adjustments and/or use any of the close-loop control systems described above.

In some embodiments, the system comprises multiple arrays of nozzles for printing multiple layers of a pharmaceutical unit. Each of the arrays of nozzles can be tuned in accordance with the steps described above. The system can comprise a controller to coordinate the operation of the multiple arrays to 3D print a batch of pharmaceutical dosage units.

The various controllers used in the printing system can comprise programmable logic controllers (PLC) which, for example, comprise a proportional-integral-derivative (PID) controller, a bang-bang controller, a predictive controller, a fuzzy control system, an expert system controller, or any other suitable controller. Further, bus structure can be used in some embodiments. The feedback system can use proportional integral differential control, bang-bang control, predictive control, fuzzy control systems, expert control, or any other appropriate control logic.

Figure 6B:
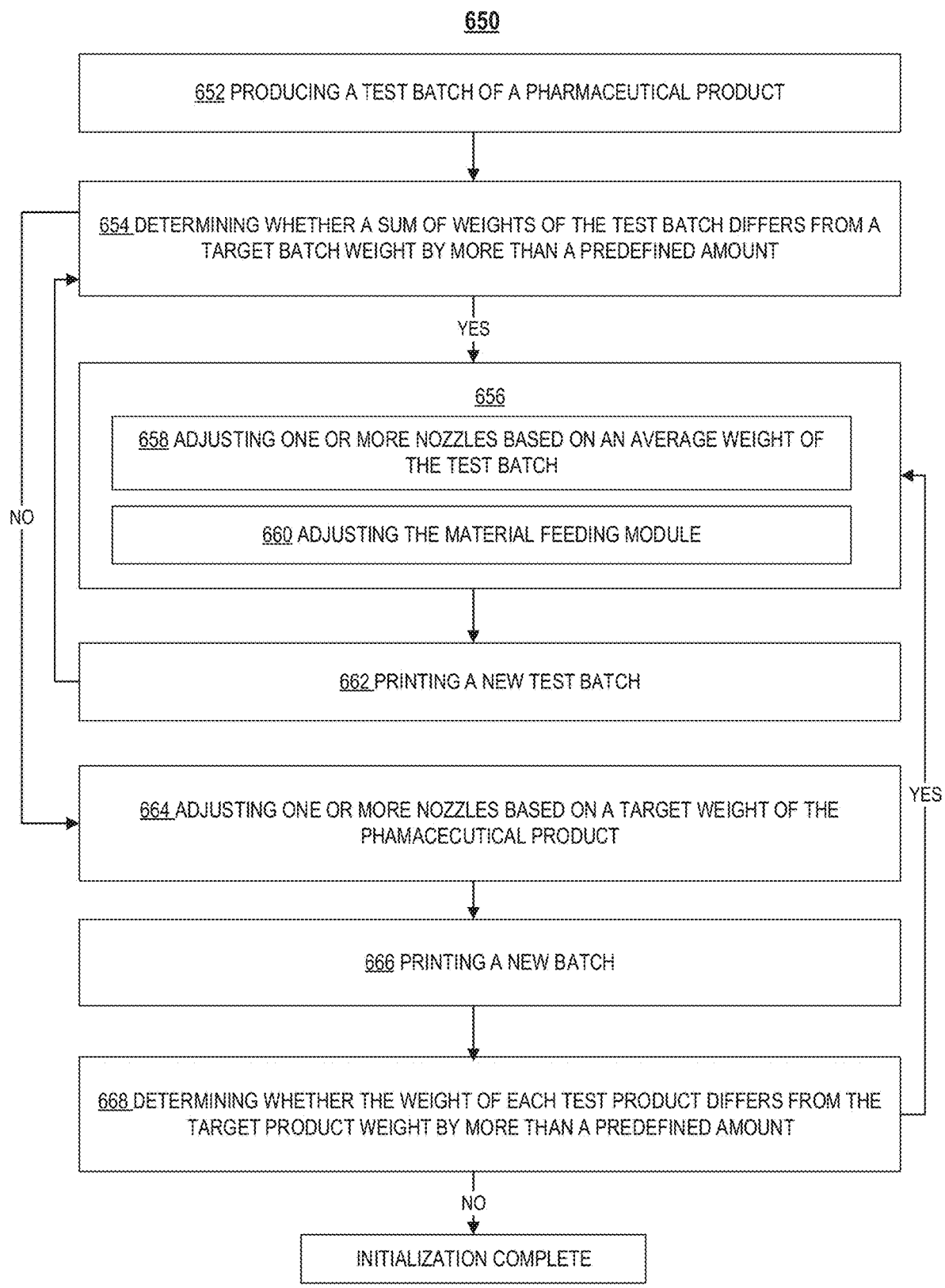
FIG. 6B depicts an exemplary process for 3D printing pharmaceutical dosage units, according to some embodiments of a present invention.

The operations described above with reference to FIGS. 5A-B are optionally implemented by components depicted in FIG. 6. It would be clear to a person having ordinary skill in the art how other processes are implemented based on the components depicted in FIG. 6.

An exemplary system for creating pharmaceutical products by additive manufacturing, comprises: a material supply module for receiving a set of printing materials; a flow distribution module comprising a flow distribution plate, wherein the material supply module is configured to transport a single flow corresponding to the set of printing materials to the flow distribution plate; wherein the flow distribution plate comprises a plurality of channels for dividing the single flow into a plurality of flows; a plurality of nozzles; and one or more controllers for controlling the plurality of nozzles to dispense the plurality of flows based on a plurality of nozzle-specific parameters.

In some embodiments, the system further comprises a printing platform configured to receive the dispensed plurality of flows, wherein the printing platform is configured to move to form a batch of the pharmaceutical product.

In some embodiments, the material supply module is configured to heat the received set of printing materials.

In some embodiments, the material supply module is configured to plasticize the received set of printing materials.

In some embodiments, the material supply module comprises a piston mechanism, a screw mechanism, a screw pump mechanism, a cogwheel mechanism, a plunger pump mechanism or any combination thereof.

In some embodiments, the plurality of channels forms a first juncture configured to dividing the single flow into two flows.

In some embodiments, wherein the plurality of channels forms a second juncture and a third juncture configured to divide the two flows into 4 flows.

In some embodiments, the first juncture is positioned higher than the second juncture and the third juncture.

In some embodiments, the first juncture, the second juncture, and the third juncture are positioned on a same plane.

In some embodiments, the flow distribution plate is splittable into a plurality of components, wherein the plurality of components are configured to be held together via one or more screws.

In some embodiments, a nozzle of the plurality of nozzles comprises a heating device.

In some embodiments, the plurality of nozzles comprises a plurality of needle-valve mechanisms.

In some embodiments, a needle-valve mechanism of the plurality of needle-valve mechanisms comprises: a feed channel extending through the respective nozzle, wherein the feed channel is tapered at a distal end of the nozzle; and a needle, wherein a distal end of the needle is configured to be in contact and seal the feed channel when the needle-valve mechanism is in a closed position, and wherein the distal end of the needle is configured to be retracted to allow a flow of printing materials to be dispensed.

In some embodiments, movement of the needle is driven by one or more motors.

In some embodiments, the one or more motors include a linear motor.

In some embodiments, movement of the needle is controlled manually.

In some embodiments, a parameter of the plurality of nozzle-specific parameters comprises an amount of opening of a respective nozzle.

In some embodiments, the one or more controllers are configured to adjust the amount of opening of the respective nozzle based on a weight of a unit in the batch corresponding to the respective nozzle.

In some embodiments, the one or more controllers are configured to adjust the amount of opening of the respective nozzle based one or more machine learning algorithms.

In some embodiments, the one or more controllers are configured to control temperature or pressure at the plurality of the nozzles.

In some embodiments, the temperature is controlled via a heating device and a temperature control device.

In some embodiments, a temperature at the plurality of the nozzles is higher than a temperature at the materials supply module.

In some embodiments, a temperature at the plurality of the nozzles is higher than a temperature at the flow distribution plate.

In some embodiments, the one or more controllers are configured to control a feeding speed of the set of printing materials.

In some embodiments, the plurality of nozzles is a first plurality of nozzles, the printing system further comprising a second plurality of nozzles configured to dispense a different set of materials, wherein the printing system is configured to switch between the first plurality of nozzles and the second plurality of nozzles to print the batch.

In some embodiments, the pharmaceutical unit is a tablet.

An exemplary computer-enabled method for creating pharmaceutical products by additive manufacturing, comprises: receiving a plurality of unit measurements corresponding to a plurality of pharmaceutical dosage units, wherein the plurality of pharmaceutical dosage units are generated using a plurality of nozzles of an additive manufacturing system; determining whether a sum of the plurality of unit measurements differs from a target batch measurement by more than a predefined threshold; in accordance with a determination that the sum differs from the target batch measurement by more than the predefined threshold, adjusting one or more nozzles of the plurality of nozzles based on an average of the plurality of unit measurements; in accordance with a determination that the sum does not differ from the target batch measurement by more than the predefined threshold, adjusting one or more nozzles of the plurality of nozzles based on a target unit measurement.

In some embodiments, the plurality of pharmaceutical unit is a plurality of tablets.

In some embodiments, the unit measurements are weight measurements of the plurality of pharmaceutical dosage units.

In some embodiments, the unit measurements are volume measurements of the plurality of pharmaceutical dosage units.

In some embodiments, the unit measurements are composition measurements of the plurality of pharmaceutical dosage units.

In some embodiments, the method further comprises: in accordance with a determination that the sum differs from the target batch measurement by more than the predefined threshold, adjusting one or more operation parameters of the additive manufacturing system.

In some embodiments, the one or more operation parameters include temperature.

In some embodiments, the one or more operation parameters include pressure.

In some embodiments, the one or more operation parameters include a speed of feeding printing materials.

In some embodiments, the predefined threshold is between +/−0.5% to +/−5%.

In some embodiments, the method further comprises, after adjusting one or more nozzles of the plurality of nozzles based on a target unit measurement, printing a new batch; determining whether a weight of an unit in the new batch differs from the target unit measurement by more than a second predefined threshold.

In some embodiments, the second predefined threshold is less than 5%.

An exemplary method for manufacturing pharmaceutical products by additive manufacturing comprises: receiving, using a material supply module, a set of printing materials; transporting, using the material supply module, a single flow corresponding to the set of printing materials to a flow distribution plate, wherein the flow distribution plate comprises a plurality of channels; dividing, via the plurality of channels of the flow distribution plate, the single flow into a plurality of flows; causing a plurality of nozzles to dispense the plurality of flows based on a plurality of nozzle-specific parameters.

An exemplary non-transitory computer-readable storage medium stores one or more programs, the one or more programs comprising instructions, which when executed by one or more processors of an electronic device having a display, cause the electronic device to: receive a plurality of weight measurements corresponding to a plurality of pharmaceutical dosage units, wherein the plurality of pharmaceutical dosage units are generated using a plurality of nozzles of a 3D printing system; determine whether a sum of the plurality of weight measurements differs from a target batch weight by more than a predefined threshold; in accordance with a determination that the sum differs from the target batch weight by more than the predefined threshold, adjust one or more nozzles of the plurality of nozzles based on an average weight measurement of the plurality of weight measurements; in accordance with a determination that the sum does not differ from the target batch weight by more than the predefined threshold, adjust one or more nozzles of the plurality of nozzles based on a target weight measurement.

Figure 7:
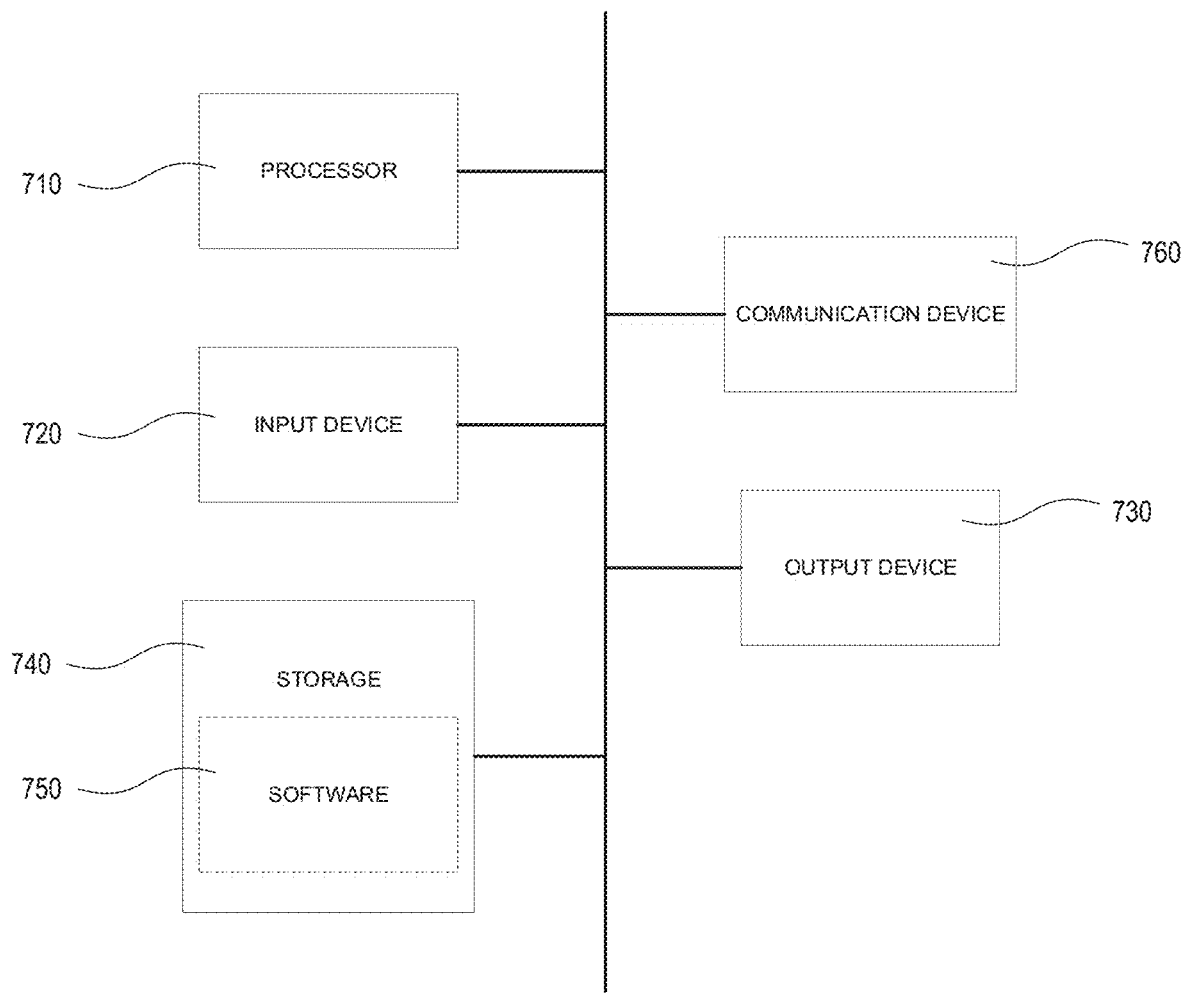
FIG. 7 depicts an exemplary electronic device in accordance with some embodiments.

FIG. 7 illustrates an example of a computing device in accordance with one embodiment. Device 700 can be a host computer connected to a network. Device 700 can be a client computer or a server. As shown in FIG. 7, device 700 can be any suitable type of microprocessor-based device, such as a personal computer, workstation, embedded system, PLC, FPGA, server or handheld computing device (portable electronic device) such as a phone or tablet. The device can include, for example, one or more of processor 710, input device 720, output device 730, storage 740, and communication device 760. Input device 720 and output device 730 can generally correspond to those described above, and can either be connectable or integrated with the computer.

Input device 720 can be any suitable device that provides input, such as a touch screen, keyboard or keypad, mouse, or voice-recognition device. Output device 730 can be any suitable device that provides output, such as a touch screen, haptics device, or speaker.

Storage 740 can be any suitable device that provides storage, such as an electrical, magnetic or optical memory including a RAM, cache, hard drive, or removable storage disk. Communication device 760 can include any suitable device capable of transmitting and receiving signals over a network, such as a network interface chip or device. The components of the computer can be connected in any suitable manner, such as via a physical bus or wirelessly.

Software 750, which can be stored in storage 740 and executed by processor 710, can include, for example, the programming that embodies the functionality of the present disclosure (e.g., as embodied in the devices as described above).

Software 750 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 740, that can contain or store programming for use by or in connection with an instruction execution system, apparatus, or device.

Software 750 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 700 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 700 can implement any operating system suitable for operating on the network. Software 750 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Figure 8A:
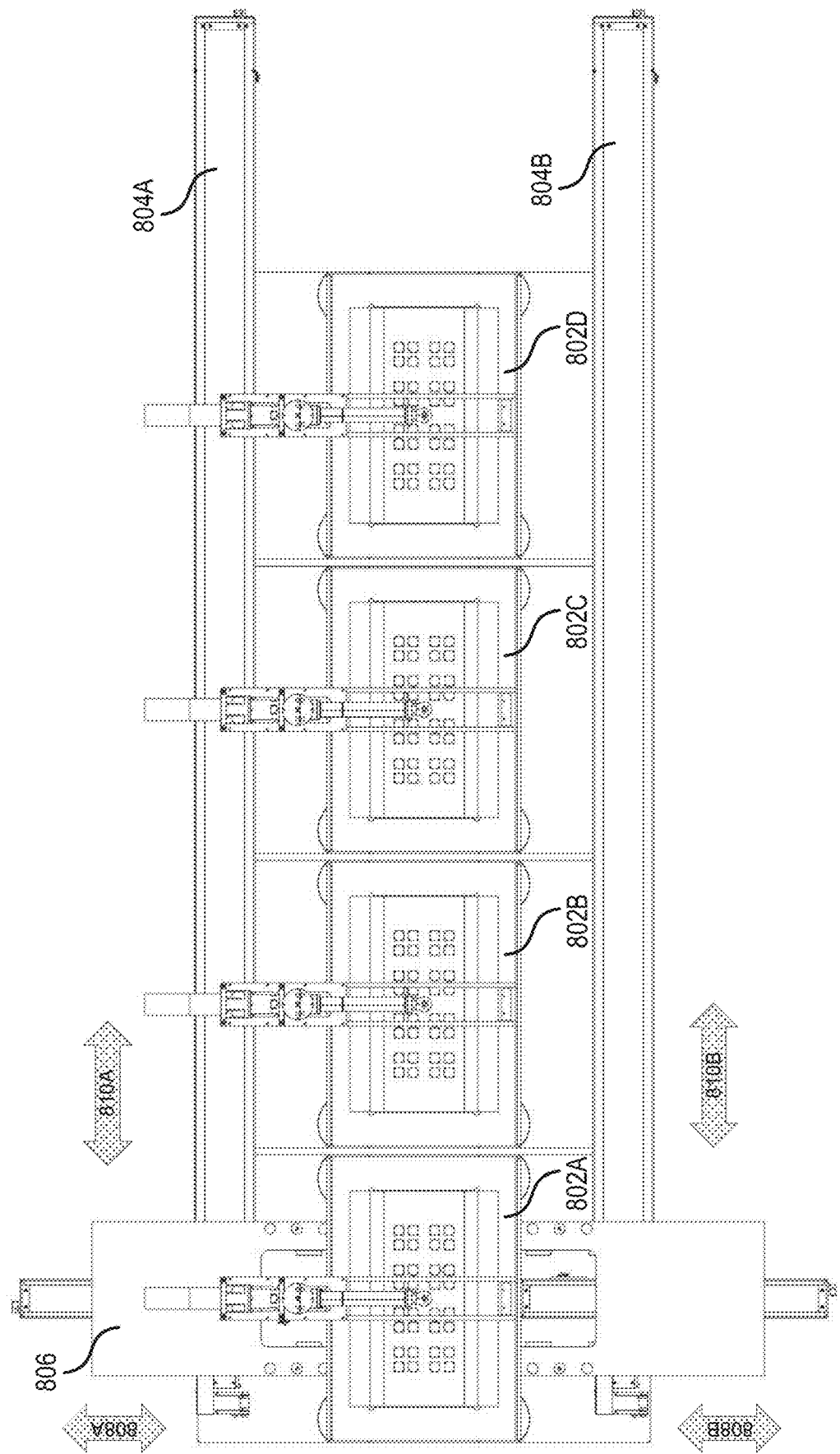
FIG. 8A depicts an exemplary layout of a standardized multi-station printing system for pharmaceutical units, in accordance with some embodiments.

FIG. 8A depicts an exemplary layout of a standardized multi-station printing system for pharmaceutical units, in accordance with some embodiments. With reference to FIG. 8, the multi-station printing system 800 comprises a plurality of printing stations 802A, 802B, 802C, and 802D. The plurality of printing stations are arranged in a linear fashion. In the top-down view depicted in FIG. 8A, each of stations 802A-802D comprises a set of nozzles (32 nozzles), which are configured to dispense multiple flows of printing materials over a printing plate to print a batch of pharmaceutical dosage units (e.g., a batch of tablets).

In some embodiments, each of the printing stations 802A-802D is configured to move a printing plate along a x-axis, a y-axis, and a z-axis with reference to a corresponding coordinate system. In some embodiments, the coordinate systems of printing stations 802A-D are different from each other, thus allowing the printing stations 802A-D to be controlled independently (e.g., via one or more controllers).

Further with reference to FIG. 8, the multi-station system 800 comprises a plate transport mechanism 806. As depicted, the plate transport mechanism 806 is configured to travel along the channels 804A and 804B. The plate transport mechanism 806 is configured to operate with the printing stations to move a printing plate off one printing station (e.g., 802A) onto one of the two ends of the plate transport mechanism (as shown by arrows 808A and 808B), transport the printing plate along either channel (as shown by arrows 810A and 810B), and move the printing plate onto another printing station. In some embodiments, the operations of the printing stations and the plate transport mechanisms are coordinated to maximize manufacturing rate and minimize idle time of the printing stations.

The multiple stations in the system 806 can be arranged in other layouts. In some embodiments, the multiple stations can be arranged around a circle or a square.

In some embodiments, the plate transport mechanism can comprise of one or more channels that are of a circular shape or square shape such that it can transport printing plates from one printing station to another. In some embodiments, the plate transport mechanism comprises one or more grippers and/or robotic arms for picking up a printing plate from one printing station and moving the printing plate to another printing station.

Figure 8B:
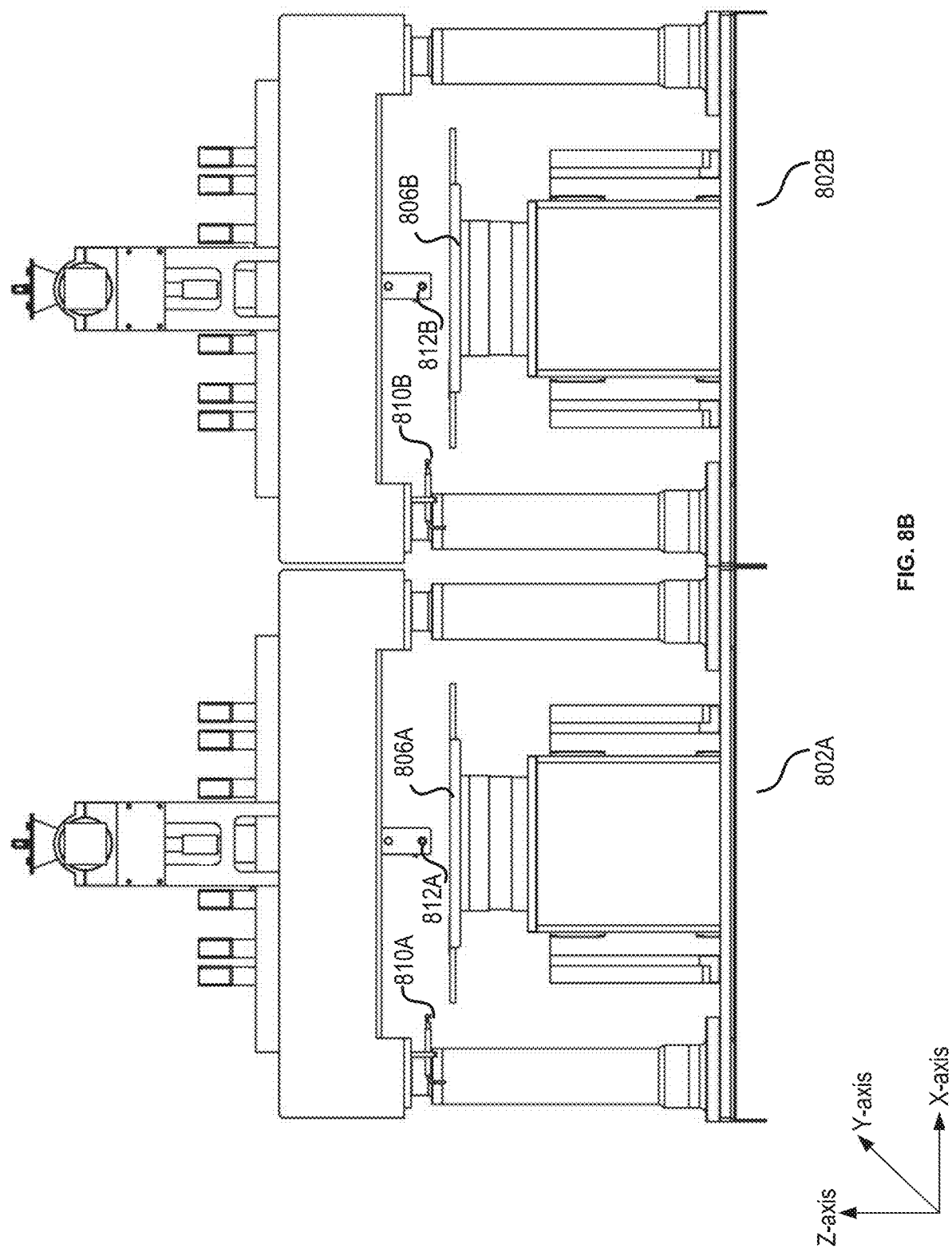
FIG. 8B depicts a partial side view of the exemplary multi-station system 800, in accordance with some embodiments.

FIG. 8B depicts a partial side view of the exemplary multi-station system 800, in accordance with some embodiments. The multi-station system 800 comprises multiple printing stations, including printing station 802A and 802B. Printing station 802A comprises a printing platform 806A and a set of nozzles (e.g., an array of nozzles) placed over the printing platform. During operation, the set of nozzles can simultaneously dispense a set of flows of printing material onto a printing plate placed on the printing platform 806A to form a batch of pharmaceutical dosage units. Printing station 802B comprises a different set of one or more nozzles and operates in a similar manner as the printing station 802B. In some embodiments, the printing stations 802A and 802B work in concert to manufacture the same batch of pharmaceutical dosage units. For example, at t0, the printing station 802A prints a batch of shells of the pharmaceutical dosage units over a plate placed on the printing platform 806A. The plate is then transported to the printing station 802B (e.g., via a plate transport mechanism) and placed onto the printing platform 806B. At t1, the printing station 802B prints the inner components within the batch of shells.

In some embodiments, the relative positioning (e.g., in the x-axis direction, in the y-axis direction, in the z-axis direction) between the printing platform and the nozzles varies from printing station to printing station. This causes the relative positioning between the pharmaceutical dosage units and the nozzles to vary from printing station to printing station. For example, the nozzles of the printing station 802A and the printing platform 806A may be centrally aligned, while the nozzles of the printing station 802B and the printing platform 806B may not be centrally aligned. In this scenario, when the plate is transported from printing station 802A to printing station 802B, the batch of shells are not perfectly aligned with the nozzles of the printing station 802A, and the system needs to account for the misalignment in the printing instructions in order to move the printing platform accordingly to print the inner components within the batch of shells.

Thus, in order to achieve high-precision printing of the same batch of pharmaceutical dosage products across multiple printing stations, the system need to acquire the relative positioning between the printing platform and the nozzles for each printing station. Based on how the relative positioning differs among the printing stations, the system can adjust the printing instruction on a given printing station to move the printing platform/printing plate accordingly such that the set of nozzles can dispense printing material at the appropriate position on the printing plate.

Figure 9:
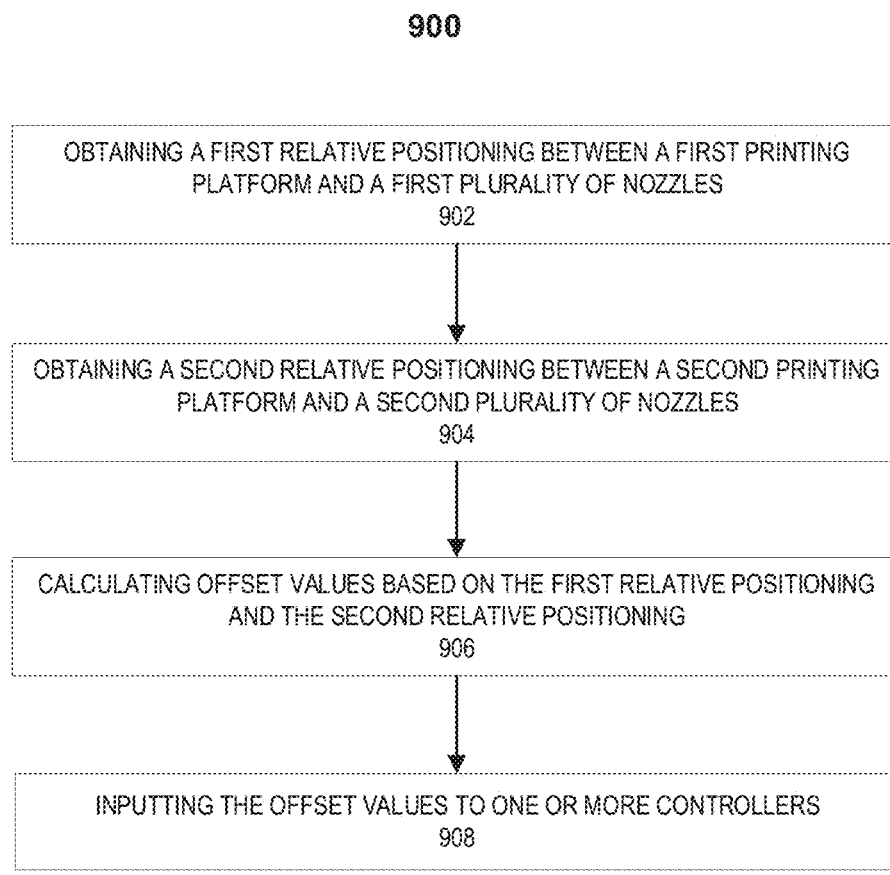
FIG. 9 depicts an exemplary process for initializing a multi-station printing system having a first printing station and a second printing station, in accordance with some embodiments.

FIG. 9 depicts an exemplary process for initializing a multi-station printing system having a first printing station and a second printing station, in accordance with some embodiments. In process 900, some blocks are, optionally, combined, the order of some blocks is, optionally, changed, and some blocks are, optionally, omitted. In some examples, additional steps may be performed in combination with the process 900. Accordingly, the operations as illustrated (and described in greater detail below) are exemplary by nature and, as such, should not be viewed as limiting.

A plate is placed onto the printing platform of the first printing station (e.g., printing platform 806A). In some embodiments, the plate is attached to the printing platform 806A via one or more pins to prevent relative movement between the plate and the printing platform 806A. In some embodiments, one or more magnetic components (e.g., electromagnetic components) of adjustable strength can be used to ensure that the plate is securely attached to the printing platform.

At block 902, after the plate is attached onto the first printing platform (e.g., 806A), the system obtains the relative positioning between the first printing platform (e.g., 806A) and the nozzles of the first printing station (e.g., 802A). In some embodiments, the relative positioning comprises a first value indicative of the relative positioning on the x-axis and a second value indicative of the relative positioning on the y-axis value.

In some embodiments, obtaining the relative positioning comprises moving the printing platform to measure the first value and the second value. With reference to FIG. 8B, the printing station 802A comprises a sensor module 810A and a sensor module 812A, which are affixed to the chassis of the printing station 802A and thus always remain stationary with respect to the nozzles. During the initialization process, the system can cause the printing platform 806A to move on the x-axis until it is in contact with the sensor 810A (e.g., based on the output of the sensor 810A). In accordance with a determination that the printing platform 806A is in contact with the sensor 810A, the system obtains the amount of movement (X1) of the printing platform 806A on the x-axis from its initial position.

The system can further cause the printing platform 806A to move on the y-axis direction until it is in contact with the sensor 812A (e.g., based on the output of the sensor 812A). In accordance with a determination that the printing platform 806A is in contact with the sensor 812A, the system obtains the amount of movement (Y1) of the printing platform 806A on the x-axis from its initial position. In some embodiments, the sensor 810A and the sensor 812A can be any type of suitable sensor, such as a position sensor or a displacement sensor.

At block 904, the system obtains the relative positioning between the second printing platform (e.g., 806B) and the nozzles of the second printing station (e.g., 802B). In some embodiments, the same plate used in block 902 is used in block 904; in some embodiments, a different plate is used. In some embodiments, no plates are placed on the first and second printing platforms.

With reference to FIG. 8B, the printing station 802B comprises a sensor module 810B and a sensor module 812B, which are affixed to the chassis of the printing station 802B and thus always remain stationary with respect to the nozzles. During the initialization process, the system can cause the printing platform 806B to move on the x-axis until the platform (or the plate on the platform) is in contact with the sensor 810B (based on the output of the sensor 810A). In accordance with a determination that the printing platform 806A is in contact with the sensor 810B, the system obtains the displacement of movement (X2) of the printing platform 806A on the x-axis from its initial position.

The system can further drive the printing platform 806B to move on the y-axis until the platform (or the plate on the platform) is in contact with the sensor 812B (e.g., based on the output of the sensor 812B). In accordance with a determination that the printing platform 806A is in contact with the sensor 812B, the system obtains the displacement of movement (Y2) of the printing platform 806B on the x-axis from its initial position.

In some embodiments, instead of moving the printing platform and determining whether it is contact with a sensor to determine the values of X1, X2, Y1, and Y2, the system uses one or more retractable sensors to determine the above values (e.g., retracting the a portion of the sensor to measure the distance X1, X2, Y1, or Y2). In some embodiments, the system uses one or more laser sensors to determine the above values.

At block 906, the system calculates the offset values based on the relative positioning (between the printing platform and the nozzles) in the first printing platform and the relative positioning in the second printing platform. In some embodiments, the offset values includes an x-axis offset value $\Delta X$ and a y-axis offset value $\Delta Y$. In some embodiments, $\Delta X$ is calculated as the difference between X1 and X2 (e.g., $\Delta X = X1 - X2$). In some embodiments, $\Delta Y$ is calculated as the difference between Y1 and Y2 (e.g., $\Delta Y = Y1 - Y2$).

At block 908, the offset values are inputted into one or more controllers. The controllers are used to generate the motion of the printing platforms of the printing stations. The offset values are used such that when the plate is transported from station to station, the location of the printing platform (and thus the batch of pharmaceutical dosage units) relative to the nozzles can be accurately determined.

Blocks 902-908 are steps directed to initializing the printing stations with respect to the x-axis and the y-axis direction. In some embodiments, the system performs initialization with respect to the z-axis direction. In some embodiments, the initialization with respect to the z-axis comprises identifying the zero point on the z-axis. The zero point is the z-axis position where the printing platform and/or the printing plate comes in contact with the nozzles, which is also where the printing of the first layer occurs.

The identification of the zero point can be performed in a number of ways. In some embodiments, the zero point is measured using a plug gauge. In some embodiments, the zero point is determined by elevating the printing platform in small increments (e.g., using lower currents such as 20%-50% of the current level during normal operation, at a lower speed such as 20%-50% of the speed during normal operation) until the printing platform comes in contact with the nozzles and can no longer be elevated further. In accordance with a determination that the printing platform is in contact with the nozzles (e.g., a resistance force above a predefined threshold is detected), the system stops elevating the printing platform and sets the location of the printing platform as the zero point. In some embodiments, a sensor is affixed to the printing plate with a retractable portion of the sensor protruded out of the printing platform on the z-axis. A block is placed on the printing plate over the sensor, such that the protruded portion of the sensor is retracted. The retracted position of the sensor is recorded. During future initializations, the printing platform is elevated such that the nozzles come in contact with the protruded portion of the sensor and cause the protruded portion of the sensor to retract. When the previously recorded retracted position is detected, the system sets the location of the printing platform as the zero point on the z-axis.

Accordingly, the initialization process is complete and the printing system is ready to start printing. For example, the system can drive the first printing station to print a portion of a batch of tablets (e.g., the bottom portions of the tablets) over a printing plate, transport the printing plate to the second printing station, and cause the second printing station to print another portion of the batch of tablets (e.g., the top portions of the tablets) based at least partially on the offset values inputted at block 908. For example, the system causes the second printing platform to move based on the offset values such that the top portions of the tablets are aligned with the bottom portions of the tablets.

In some embodiments, using the techniques described herein, the derivations among the nozzles at each printing station can be within 0.01 mm (e.g., 0.02-0.05 mm) on the x-axis, within 0.01 mm (e.g., 0.02-0.05 mm) on the y-axis, and within 0.005 mm (e.g., 0.01-0.05 mm) on the z-axis. This ensures that, when a batch of pharmaceutical dosage units is transported and printed across multiple printing stations, the nozzles at each printing station can line up with the batch of pharmaceutical dosage units in an accurate manner.

In some embodiments, multiple printing plates can be used in the multi-station printing system. In some embodiments, each printing plate is placed on all printing stations to obtain a plurality of X-values (e.g., n X-values corresponding to the n printing stations), a plurality of Y-values (e.g., n Y-values corresponding to the n printing stations), and/or a plurality of Z-values (e.g., n Z-values corresponding to the n printing stations) associated with the plate. This way, the offset values between any two printing stations for the plate can be obtained such that, when the plate is moved from a first printing station to a second printing station, the offset values can be used to determine the location of the plate (and thus the batch of pharmaceutical dosage units) relative to the nozzles of the second printing station. Thus, the nozzles of the second printing station can be moved accordingly to continue printing the batch of pharmaceutical dosage units on the plate.

Figure 10A:
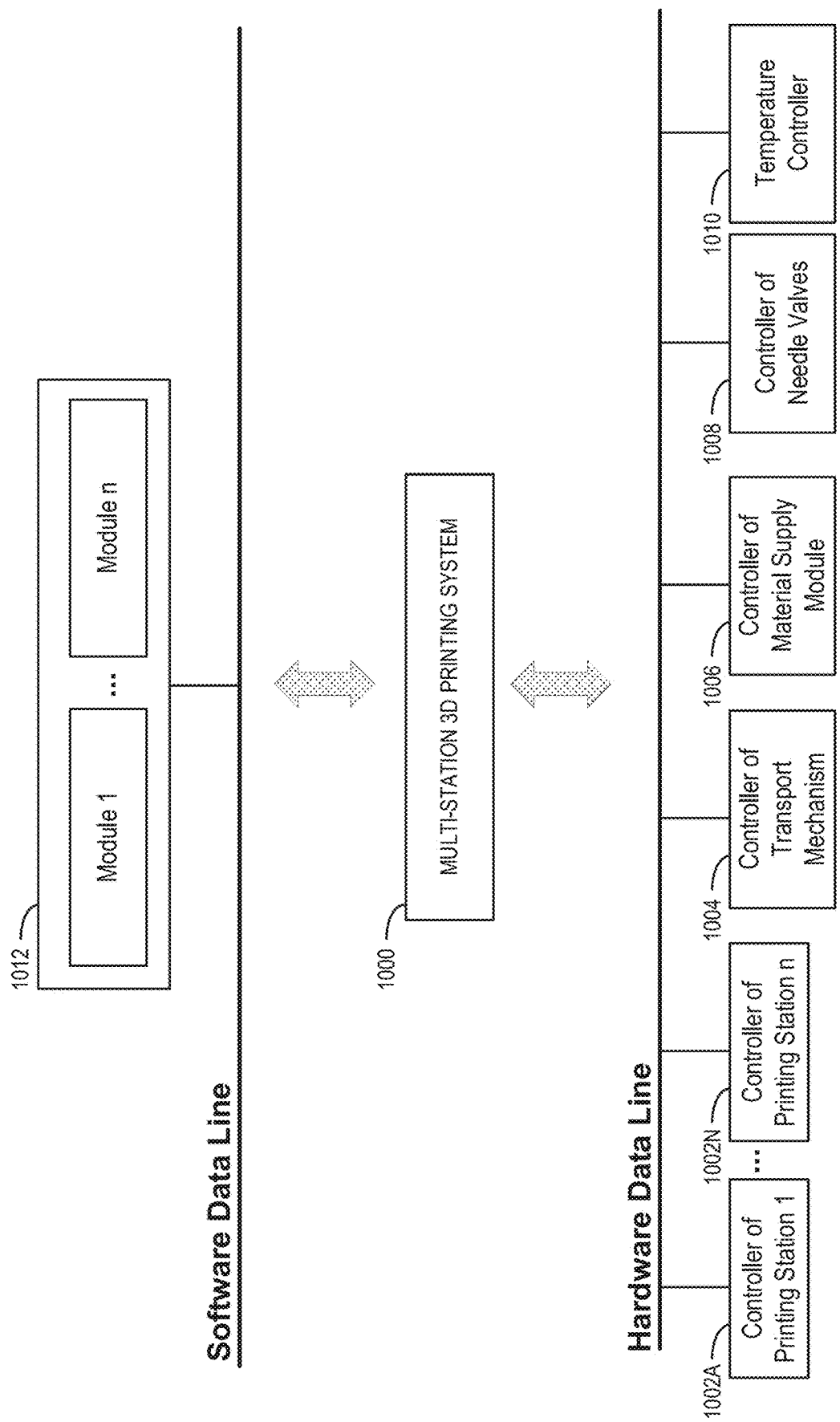
FIG. 10A depicts an exemplary architecture of a multi-station 3D printing system, in accordance with some embodiments.

FIG. 10A depicts an exemplary architecture of a multi-station 3D printing system, in accordance with some embodiments. The 3D printing system 1000 comprises a plurality of hardware components and software components, all of which can be communicatively coupled together (e.g., via communication protocols such as modbus, via one or more networks such as P2P networks) to provide a high-speed and high-throughput printing system. With reference to FIG. 10A, the system 1000 comprises a plurality of controllers 1002A-1002N, which are configured to control the movements of N printing stations, respectively. Each controller can be coupled to a set of actuator(s) and motor(s) for moving the respective printing platform of the respective printing station along the x-axis, y-axis, and z-axis. In some embodiments, a single controller can be used to control the movements of multiple printing platforms of multiple printing stations.

The system 1000 further comprises a controller 1004, which is configured to control the movement of a plate transport mechanism (e.g., 806 depicted in FIG. 8A). The controller 1004 can be coupled to a set of actuator(s) and motor(s) for moving a printing plate (e.g., along a conveyor or channel, via a gripper loader).

The system 1000 further comprises one or more controllers 1006 configured to control the feeding of the printing materials by the material supply modules (e.g., 102 depicted in FIG. 1A). The system further comprises one or more controllers 1008 configured to control the needle valves at the printing nozzles. For example, the one or more controllers 1008 can be coupled to actuator(s) and motor(s) driving the movements of the needles. The system further comprises temperature controller 1010, which is configured to control temperature at various portions of the system (e.g., flow distribution plate).

The system 1000 further comprises a plurality of software modules 1012. In some embodiments, the plurality of software modules comprises: a file management module, a process monitoring module, a modeling module, a post-processing module, a process optimization module, a simulation module, an analytic module, a speed control module, or any combination thereof.

In some embodiments, the system 1000 is communicatively coupled to one or more networks, such that it can rely on the cloud for data storage, data management, and data analytics. In some embodiments, the system 1000 is communicatively coupled to one or more mobile devices such that the printing processes can be monitored and controlled remotely. In some embodiments, the system provides a user interface (e.g., one or more graphical user interfaces) to allow a user to control and monitor the printing processes, as well as to enter and modify printing parameters (e.g., temperature, pressure, speed, needle positions and movements). In some embodiments, the system provides real-time monitoring of various parameters of the printing processes at all printing stations and all printing plates.

In some embodiments, the system 1000 comprises a quality control system for testing the printed dosage units against various metrics (e.g., shape, size, composition, consistency). In some embodiments, the system 1000 comprises additional hardware components such as sensors, cameras, and alert systems.

Figure 10C:
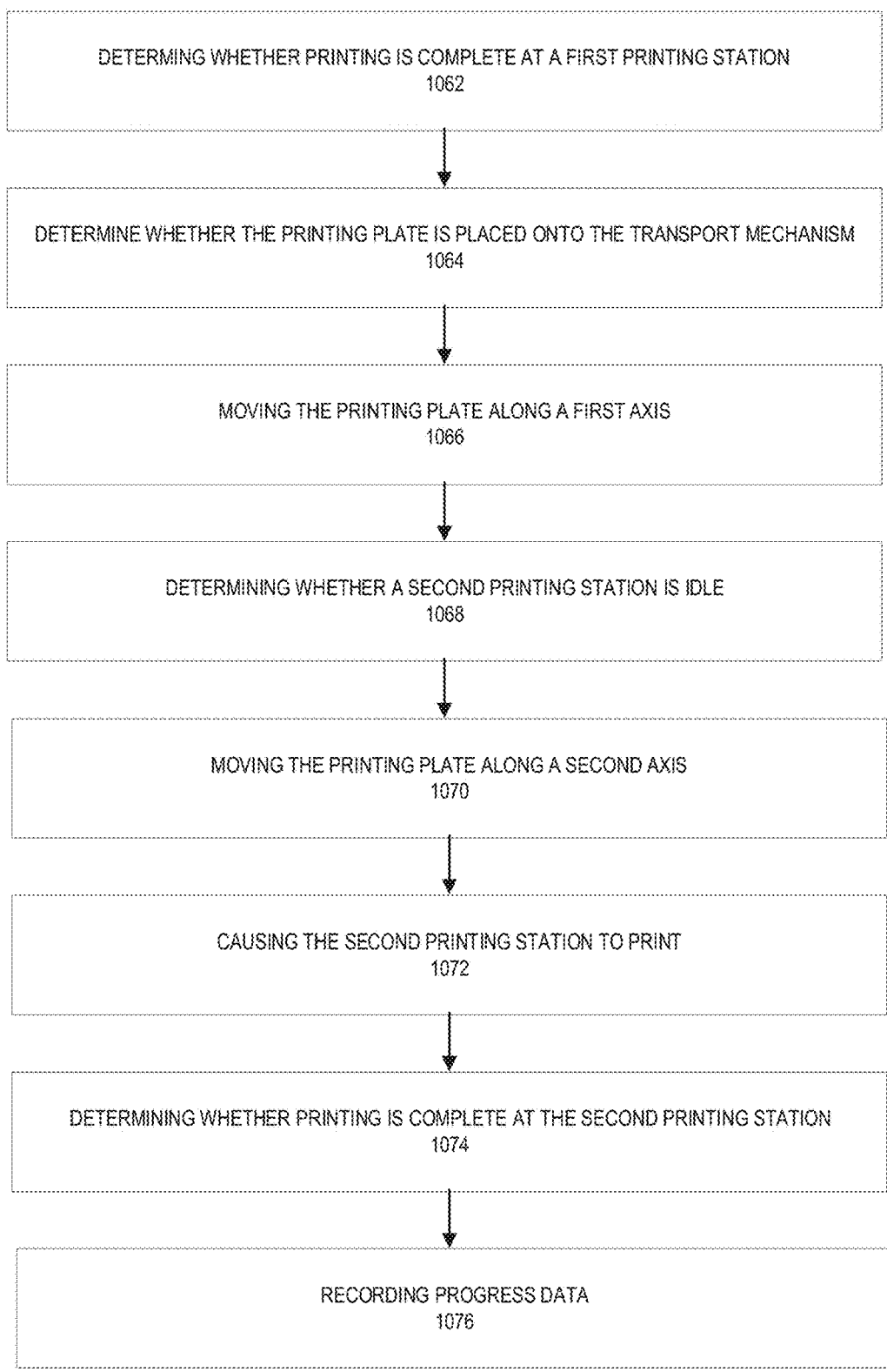
FIG. 10C depicts an exemplary process for 3D printing pharmaceutical dosage units using a multi-station system, according to some embodiments.

FIGS. 10B-C depict exemplary processes for 3D printing pharmaceutical dosage units using a multi-station system, according to some embodiments. Processes 1030 and 1060 can be part of the software modules 1012 depicted in FIG. 10A. In each process, some blocks are, optionally, combined, the order of some blocks is, optionally, changed, and some blocks are, optionally, omitted. In some examples, additional steps may be performed in combination with each process. Accordingly, the operations as illustrated (and described in greater detail below) are exemplary by nature and, as such, should not be viewed as limiting.

Process 1030 can be performed at a printing station of the multi-station system. At block 1032, the system mounts a printing plate onto a printing platform of the printing station. Optionally, at block 1034, the system moves the printing platform to a receiving position (e.g., by lowering the printing platform along the z-axis) such that the printing plate can be moved from the plate transport mechanism onto the printing platform (e.g., along the y-axis direction by the plate transport mechanism).

At block 1036, the system determines whether the plate aligned with the platform. In some embodiments, the system makes the determination based on inputs from one or more sensors. In some embodiments, the system determines that the plate is placed onto the platform if a proper alignment between components of the plate and components of the platform (e.g., pins) is detected.

At block 1038, in accordance with a determination that the plate is placed onto the platform, the system couples the plate and the platform. In some embodiments, the system performs the coupling by raising the printing platform along the z-axis such that the printing plate comes in contact with the printing platform. In some embodiments, the system activates one or more electromagnetic components to ensure that the plate is securely attached or coupled to the platform.

At block 1040, the system identifies a portion of printing instructions based on progress data associated with the printing plate. In some embodiments, each printing station of the system has access to a copy of the same printing instructions for printing a pharmaceutical dosage unit. As such, each printing station needs to identify the portion of the printing instructions before commencing printing. In some embodiments, the progress data comprises a current height of the pharmaceutical dosage units (i.e., along the z axis), an identifier of the printing station, or a combination thereof. In some embodiments, the progress data is provided to the printing station by the plate transport mechanism.

At block 1042, the system performs 3D printing based on the identified portion of printing instructions. In some embodiments, the printing is performed based on the coordinate system associated with the current printing station, which can be obtained as discussed above with reference to FIG. 9.

In some embodiments, the system identifies the plate by scanning a code (e.g., an RFID code) on the plate. In some embodiments, the identity of the plate can be used to identify printing instructions and the coordinate system.

At block 1044, the system determines whether printing is complete based on the identified portion of printing instructions. In some embodiments, the printing instructions include one or more indicators marking the beginning and/or end of a portion of printing instructions to be performed by a particular printing station. As such, the system can determine that printing is complete upon detecting the one or more indicators marking the end of the portion of printing instructions.

At block 1046, in accordance with a determination that printing is complete at the current printing station, the system records progress data associated with the printing plate. In some embodiments, the progress data includes an identifier of the next printing station (e.g., based on the printing instructions), a current height of the pharmaceutical dosage units, or a combination thereof. In some embodiments, the current printing station records the progress data and transmits the progress data to the plate transport mechanism.

At block 1048, the system unloads the printing plate from the printing platform. In some embodiments, this includes lowering the printing platform and deactivating the electromagnetic components such that the plate transport mechanism can pick up the printing plate. In some embodiments, the current printing station is marked as idle by the station itself and/or by the system.

FIG. 10C depicts an exemplary process for 3D printing pharmaceutical dosage units using a multi-station system, according to some embodiments. Process 1060 can be performed by the plate transport mechanism. In order to coordinate the operations of multiple printing stations and the plate transport mechanism, the multi-station system tracks the status of its various components via a plurality of parameters such as: identifiers of the printing stations, locations of the printing stations, whether each printing station is busy or idle, the locations of all printing plates, the progress data (e.g., current height) associated with each printing plate, the location of the plate transport mechanism (e.g., coordinates on the channels), the coordinate systems of the printing stations, the height of all of the components (e.g., printing platforms, printing plates, plate transport mechanism), or any combination thereof. These parameters, or multiple versions of these parameters, can be store at a single location or distributed across multiple components.

At block 1062, the system determines whether printing is complete at a first printing station. The determination can be made based on the status of the first printing station (e.g., busy or idle) or based on signals transmitted from the first printing station to the plate transport mechanism.

At block 1064, in accordance with a determination that printing is complete at the first printing station, the system determines whether the printing plate is placed onto the plate transport mechanism. As discussed above with respect to FIG. 10B, after the printing is complete, the printing station can decouple the printing plate from the printing platform. Subsequently, the plate transport mechanism can pick up the printing plate and move the printing plate off the printing platform.

At block 1066, the system moves the printing plate along a first axis (e.g., the x-axis). For example, as depicted in FIGS. 8A and 8B, the system can move the printing plate along a conveyor along the x-axis until the printing plate is beside the second printing station. In some embodiments, the second printing station is determined by the plate transport mechanism based on the progress data generated in block 1046. In some embodiments, the second printing station is determined by the system based on the status and the printing materials at each printing station (e.g., selecting an idle station that can dispense the current printing materials needed for the products on the printing plate).

At block 1068, the system determines whether the second printing station is idle, for example, based on the status parameter of the second printing station (e.g., stored on the second printing station, stored on system-wide memory). At block 1070, in accordance with a determination that the second printing station is idle, the system moves the printing plate along a second axis (e.g., the y-axis) toward the second printing station. In some embodiments, the plate transport mechanism notifies the second printing station, which proceeds to mount the printing plate onto its printing platform as discussed above. In some embodiments, the second printing station is marked as busy. The status of the second printing station can be stored locally at the second printing station, at the plate transport mechanism, and/or at a system-wide memory.

At block 1072, the system causes the second printing station to perform 3D printing over the printing plate. The second printing station can perform the process 1030, including receiving progress data (e.g., from the plate transport mechanism and identifying a portion of printing instructions).

At block 1074, the system determines whether printing is complete at the second printing station. The determination can be made based on the status of the second printing station (e.g., busy or idle) or based on signals transmitted from the second printing station to the plate transport mechanism. In accordance with a determination that printing is complete at the second printing station, the system determines whether the printing plate is placed onto the plate transport mechanism. As discussed above with respect to FIG. 10B, after the printing is complete, the second printing station can decouple the printing plate from the printing platform. Subsequently, the plate transport mechanism can pick up the printing plate and move the printing plate off the printing platform.

At block 1076, the system records progress data associated with the printing plate. Progress data can comprise the current height of the pharmaceutical dosage units on the printing plate. In some embodiments, the progress data is determined by the second printing station based on the printing instructions, and transmitted from the second printing station to the plate transport mechanism. In some embodiments, the plate transport mechanism can transmit the progress data to the next printing station. In some embodiments, the entire multi-station system stores one copy of the progress data associated with the printing plate, and various components of the system (e.g., plate transport mechanism, stations) have access to the progress data.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

What is claimed is:

1. A system for creating pharmaceutical products by additive manufacturing, comprising:
   a material supply module for receiving a set of printing materials for creating the pharmaceutical products;
   a flow distribution module comprising a flow distribution plate,
      wherein the material supply module is configured to transport a single flow corresponding to the set of printing materials to the flow distribution plate;
      wherein the flow distribution plate comprises: a plurality of channels for dividing the single flow into a plurality of flows;
   a plurality of nozzles; and
   one or more controllers for controlling the plurality of nozzles to dispense the plurality of flows based on a plurality of nozzle-specific parameters to create the pharmaceutical products, wherein the set of printing materials for creating the pharmaceutical products is heated to a first temperature in the flow distribution plate and heated to a second temperature higher than the first temperature in the plurality of nozzles.

2. The system of claim 1, further comprising a printing platform configured to receive the dispensed plurality of flows, wherein the printing platform is configured to move to form the pharmaceutical products.

3. The system of claim 1, wherein the material supply module is configured to plasticize the received set of printing materials and wherein the material supply module comprises a piston mechanism, a screw mechanism, a screw pump mechanism, a cogwheel mechanism, a plunger pump mechanism or any combination thereof.

4. The system of claim 1, wherein the plurality of channels forms a first juncture configured to divide the single flow into two flows.

5. The system of claim 4, wherein the plurality of channels forms a second juncture and a third juncture configured to divide the two flows into 4 flows.

6. The system of claim 1, wherein the flow distribution plate is split-able into a plurality of components to expose inner surfaces of the plurality of channels, wherein the plurality of components are configured to be held together via one or more screws.

7. The system of claim 1, wherein a nozzle of the plurality of nozzles comprises a heater, or wherein a nozzle of the plurality of nozzles comprises a thermal isolation structure.

8. The system of claim 1, wherein the plurality of nozzles comprises a plurality of needle-valve mechanisms, and wherein a needle-valve mechanism of the plurality of needle-valve mechanisms comprises:
a feed channel extending through the respective nozzle, wherein the feed channel is tapered at a distal end of the nozzle; and
a needle, wherein a distal end of the needle is configured to be in contact and seal the feed channel when the needle-valve mechanism is in a closed position, and wherein the distal end of the needle is configured to be retracted to allow a flow of printing materials to be dispensed.

9. The system of claim 8, wherein movement of the needle is driven by one or more actuators, or wherein the one or more actuators include a linear motor.

10. The system of claim 8, wherein the needle is a first needle, wherein the plurality of nozzles comprises a single plate coupled to the first needle and a second needle, and wherein movement of the single plate causes movement of the first needle and the second needle.

11. The system of claim 8, wherein the diameter of the plurality of channels of the flow distribution plate is larger than the diameter of feed channels of the plurality of nozzles.

12. The system of claim 11, wherein the material supply module is configured to transport the single flow to the flow distribution plate via a supply channel, and wherein the diameter of the supply channel is larger than the diameter of the plurality of channels of the flow distribution plate.

13. The system of claim 1, wherein a parameter of the plurality of nozzle-specific parameters comprises an amount of opening of a respective nozzle.

14. The system of claim 13, wherein the one or more controllers are configured to adjust the amount of opening of the respective nozzle based on a weight of a pharmaceutical product corresponding to the respective nozzle.

15. The system of claim 1, wherein the one or more controllers are configured to control temperature or pressure at the plurality of the nozzles.

16. The system of claim 1, wherein a temperature at the plurality of the nozzles is higher than a temperature at the materials supply module, or wherein a temperature at the plurality of the nozzles is higher than a temperature at the flow distribution plate.

17. The system of claim 1, wherein flow paths of the plurality of flows are geometrically symmetrical.

18. The system of claim 1, wherein the flow distribution plate is split-able and comprises a plurality of modules, wherein each module of the plurality of modules is configured to receive a flow and divide the flow into four flows to be dispensed by four nozzles of the plurality of nozzles.

19. A method for creating pharmaceutical products by additive manufacturing, comprising:
receiving, by a material supply module, a set of printing materials for creating the pharmaceutical products;
transporting a single flow corresponding to the set of printing materials to a flow distribution module comprising a flow distribution plate;
dividing, by a plurality of channels of the flow distribution plate, the single flow into a plurality of flows, wherein the set of printing materials is heated to a first temperature in the flow distribution plate;
receiving, by a plurality of nozzles, the plurality of flows;
heating, in the plurality of nozzles, the set of printing materials to a second temperature higher than the first temperature; and
controlling, by one or more controllers, the plurality of nozzles to dispense the plurality of flows based on a plurality of nozzle-specific parameters to create the pharmaceutical products.

20. The method of claim 19, further comprising:
receiving, by a printing platform, the dispensed plurality of flows, and
moving the printing platform to form the pharmaceutical products.

21. The method of claim 19, wherein the flow distribution plate is split-able into a plurality of components to expose inner surfaces of the plurality of channels, wherein the plurality of components are configured to be held together via one or more screws.

22. The method of claim 19, wherein the plurality of nozzles comprises a plurality of needle-valve mechanisms, and wherein a needle-valve mechanism of the plurality of needle-valve mechanisms comprises:
a feed channel extending through the respective nozzle, wherein the feed channel is tapered at a distal end of the nozzle; and
a needle, wherein a distal end of the needle is configured to be in contact and seal the feed channel when the needle-valve mechanism is in a closed position, and wherein the distal end of the needle is configured to be retracted to allow a flow of printing materials to be dispensed.

23. The method of claim 22, wherein the diameter of the plurality of channels of the flow distribution plate is larger than the diameter of feed channels of the plurality of nozzles.

24. The method of claim 23, wherein the material supply module is configured to transport the single flow to the flow distribution plate via a supply channel, and wherein the diameter of the supply channel is larger than the diameter of the plurality of channels of the flow distribution plate.

25. The method of claim 19, wherein a parameter of the plurality of nozzle-specific parameters comprises an amount of opening of a respective nozzle.

26. The method of claim 25, further comprising: adjusting, by the one or more controllers, the amount of opening of the respective nozzle based on a weight of a pharmaceutical product corresponding to the respective nozzle.

27. The method of claim 19, further comprising: controlling, by the one or more controllers, temperature or pressure at the plurality of the nozzles.

28. The method of claim 19, wherein a temperature at the plurality of the nozzles is higher than a temperature at the materials supply module.

29. The method of claim 19, wherein flow paths of the plurality of flows are geometrically symmetrical.

30. The method of claim 19, wherein the flow distribution plate is split-able and comprises a plurality of modules, wherein each module of the plurality of modules is configured to receive a flow and divide the flow into four flows to be dispensed by four nozzles of the plurality of nozzles.

\* \* \* \* \*